US010894962B2

(12) United States Patent
Panzner

(10) Patent No.: US 10,894,962 B2
(45) Date of Patent: Jan. 19, 2021

(54) CARBOXYLATED 2'-AMINO-LNA NUCLEOTIDES AND OLIGONUCLEOTIDES COMPRISING THE SAME

(71) Applicant: BioNTech Delivery Technologies GmbH, Halle (DE)

(72) Inventor: Steffen Panzner, Halle (DE)

(73) Assignee: BIONTECH DELIVERY TECHNOLOGIES GMBH, Halle (DE)

( * ) Notice: Subject to any disclaimer, the term of this patent is extended or adjusted under 35 U.S.C. 154(b) by 0 days.

(21) Appl. No.: 16/325,827

(22) PCT Filed: Aug. 11, 2017

(86) PCT No.: PCT/EP2017/070492
§ 371 (c)(1),
(2) Date: Feb. 15, 2019

(87) PCT Pub. No.: WO2018/033492
PCT Pub. Date: Feb. 22, 2018

(65) Prior Publication Data
US 2019/0203208 A1   Jul. 4, 2019

(30) Foreign Application Priority Data

Aug. 16, 2016  (EP) ..................... 16184362

(51) Int. Cl.
C07H 19/06 (2006.01)
C07H 19/16 (2006.01)
C12N 15/11 (2006.01)
C12N 15/113 (2010.01)
C07H 21/00 (2006.01)
C07H 19/10 (2006.01)

(52) U.S. Cl.
CPC ........... C12N 15/113 (2013.01); C07H 19/06 (2013.01); C07H 19/10 (2013.01); C07H 19/16 (2013.01); C07H 21/00 (2013.01); C12N 15/111 (2013.01); C12N 2310/11 (2013.01); C12N 2310/314 (2013.01); C12N 2310/3231 (2013.01); C12N 2310/341 (2013.01); C12N 2320/51 (2013.01); C12N 2320/52 (2013.01)

(58) Field of Classification Search
None
See application file for complete search history.

(56) References Cited

U.S. PATENT DOCUMENTS

| 6,670,461 | B1 | 12/2003 | Wengel et al. | |
| 7,569,575 | B2 | 8/2009 | Sorensen et al. | |
| 2004/0014959 | A1* | 1/2004 | Sorensen | C07H 19/04 536/26.7 |
| 2015/0368642 | A1 | 12/2015 | Albaek et al. | |

FOREIGN PATENT DOCUMENTS

| WO | WO-2008074488 A2 | 6/2008 |
| WO | WO-2010004054 A2 | 1/2010 |
| WO | WO-2014005596 A1 | 1/2014 |

OTHER PUBLICATIONS

Astakhova et al., (2014). "Scaffolding along nucleic acid duplexes using 2'-amino-locked nucleic acids," Accounts of Chemical Research, 47(6):1768-1777.
Bestas et al., (2014). "Splice-correcting oligonucleotides restore BTK function in X-linked agammaglobulinemia model," J. Clin. Investigation, 9:4067-81.
European Search Report and Written Opinion received for Patent Application No. EP17752375, dated Mar. 26, 2020, 5 pages.
Frieden et al., (2003). "Expanding the design horizon of antisense oligonucleotides with alpha-L-LNA," Nucleic Acids Res., 31:6365-6372.
International Preliminary Report on Patentability received for PCT Patent Application No. PCT/EP2017/070492, dated Feb. 19, 2019, 7 pages.
International Search Report and Written Opinion received for PCT Patent Application No. PCT/EP2017/070492, dated Feb. 22, 2018, 11 pages.
Jepsen et al., (2004). "Locked nucleic acid: a potent nucleic acid analog in therapeutics and biotechnology," J. Oligonucleotides, 14:130-146.
Johannsen et al., (2011). "Amino acids attached to 2'-amino-LNA: synthesis and excellent duplex stability", Organic & Biomolecular Chemistry, 9(1):243-252.
Koller et al., (2006). "Use of a Chemically Modified Antisense Oligonucleotide Library to Identify and Validate Eg5 (Kinesin-Like 1) as a Target for Antineoplastic Drug Development," Cancer Res., 66(4):2059-2066.
Koshkin et al., (1998). "LNA (Locked Nucleic Acids): Synthesis of the adenine, cytosine, guanine, 5-methylcytosine, thymine and uracil bicyclonucleoside monomers, oligomerisation, and unprecedented nucleic acid recognition," Tetrahedron, 54:36073630.
Kurreck et al., (2002). "Design of antisense oligonucleotides stabilized by locked nucleic acids," Nucleic Acids Res., 30:1911-1918.
Langkjaer et al., (2009). "UNA (unlocked nucleic acid): a flexible RNA mimic that allows engineering of nucleic acid duplex stability," Bioorg. Med. Chem., 17:5420-5.
Lima et al., (2004). "Structural Requirements at the Catalytic Site of the Heteroduplex Substrate for Human RNase H1 Catalysis," J. Biol. Chem., 279:36317-36326.
Lok et al., (2002). "Potent Gene-Specific Inhibitory Properties of Mixed-Backbone Antisense Oligonucleotides Comprised of 2'-Deoxy-2'-fluoro-d-arabinose and 2'-Deoxyribose Nucleotides," Biochemistry, 41:3457-3467.
Lou et al., (2015). "Oligonucleotides containing a piperazino-modified 2'-amino-LNA monomer exhibit very high duplex stability and remarkable nuclease resistance," Chemical Communications, 51(19):4024-4027.

(Continued)

Primary Examiner — Traviss C McIntosh, III
(74) Attorney, Agent, or Firm — Morrison & Foerster LLP

(57) ABSTRACT

The invention proves an oligonucleotide comprising one or more carboxylated 2'-amino-LNA nucleotide units. The invention also provides a method of transfecting cells with the oligonucleotide, a method of treating a human or animal by therapy using the oligonucleotide, and a pharmaceutical composition comprising the oligonucleotide.

20 Claims, 3 Drawing Sheets

(56) References Cited

OTHER PUBLICATIONS

Monia et al., (1993). "Evaluation of 2'-modified oligonucleotides containing 2'-deoxy gaps as antisense inhibitors of gene expression," J. Biol. Chem., 268:14514-14522.

Nielsen et al., (1999). "The solution structure of a locked nucleic acid (LNA) hybridized to DNA," J. Biomol. Struct. Dyn., 17:175-191.

Nielsen et al., (2000). "Solution Structure of an LNA Hybridized to DNA: NMR Study of the d(CTLGCTLTLCTLGC):d(GCAGAAGCAG) Duplex Containing Four Locked Nucleotides," Bioconjugate Chem., 11:228-238.

Nishiyama et al., (2003). "Differential Gene Expression Profile between PC-14 Cells Treated with Free Cisplatin and Cisplatin-Incorporated Polymeric Micelles," Bioconjugate Chem., 14:449-457.

Obika et al., (1998). "Stability and structural features of the duplexes containing nucleoside analogues with a fixed N-type conformation, 2'-0,4'-C-methyleneribonucleosides," Tetrahedron Lett., 39:5401-5404.

Petersen et al., (2002). "Locked Nucleic Acid (LNA) Recognition of RNA: NMR Solution Structures of LNA:RNA Hybrids," J. Am. Chem. Soc., 124:5974-5982.

Petersen et al., (2003). "LNA: a versatile tool for therapeutics and genomics," Trends Biotechnol., 21:74-81.

Prakash et al., (2014). "Targeted delivery of antisense oligonucleotides to hepatocytes using triantennary N-acetyl galactosamine improves potency 10-fold in mice," Nucleic Acids Res., 42:8796-8807.

Rahman et al., (2009). "Synthesis of several types of bridged nucleic acids," Chem. Lett., 38:512-17.

Sorensen et al., (2002). "Alpha-l-ribo-Configured Locked Nucleic Acid (α-L-LNA): Synthesis and Properties," J. Am. Chem. Soc., 124:2164-2176.

Sorensen et al., (2003). "Functionalized LNA (locked nucleic acid): high-affinity hybridization of oligonucleotides containing N-acylated and Nalkylated 2'-amino-LNA monomers", Chemical Communications, 17(1):2130-2131.

Umemoto et al., (2009). "Functionalization of 2'-amino-LNA with additional nucleobases," Organic & Biomolecular Chemistry, 7(9), p. 1793.

Vester et al., (2004). "LNA (locked nucleic acid): high-affinity targeting of complementary RNA and DNA," J. Biochemistry, 43, 13233-13241.

Zhou et al., (2009). "The synthesis of therapeutic locked nucleos(t)ides," J. Curr. Opin. Drug Disc. Devel., 12(6):876-98.

* cited by examiner compound 1 compound 2, x=13 compound 3, x=13 compound 4, x=13
compound 6, x=8 compound 5, x=13
compound 7, x=8 compound 8, x=13

CARBOXYLATED 2'-AMINO-LNA NUCLEOTIDES AND OLIGONUCLEOTIDES COMPRISING THE SAME

FIELD OF THE INVENTION

The invention relates to an oligonucleotide comprising one or more carboxylated 2'-amino LNA nucleotide units, such as carboxyhydrocarbyl-Z-amino LNA nucleotide units and/or carboxyheterohydrocarbyl-Z-amino LNA nucleotide units. The invention also relates to 2' carboxyalkyl- and/or carboxyaryl-2'-amino-LNA nucleotides and oligonucleotides comprising one or more of the same. The oligonucleotides of the invention have improved efficacy and specificity.

CERTAIN DEFINITIONS AND STATE OF THE ART

Oligonucleotides

Throughout this invention, oligonucleotides mean nucleic acids having internucleoside linkages, nucleoside sugars and nucleobases. The number of nucleobases within the oligonucleotides of this invention is an integer between 3 and 100 and is essentially equal to the number of nucleosides and the next integer to the number of internucleoside linkages. The oligonucleotides of the invention have from 3 to 100 nucleotides, preferably from 5 to 70 nucleotides, more preferably from 7 to 50 nucleotides, and even more preferably from 9 to 30 nucleotides. The "length" of the oligonucleotides is determined by the number of nucleotides.

The oligonucleotides of this invention can interact with intracellular nucleic acids, herein referred to as targets or target sequences. "Interact" means a process that involves binding of the oligonucleotide to the target sequence e.g. by hybridization, or it means a process that involves competition with the target sequence. In any case the specificity of the interaction is determined by the sequence of nucleobases. The sequence of an oligonucleotide is therefore non-random.

The oligonucleotides of this invention may be single-stranded. The oligonucleotides of this invention may also be double stranded or essentially double-stranded. Double stranded oligonucleotides have a complementary sequence on both of their strands; essentially double stranded oligonucleotides further comprise non-complementary regions, wherein these regions do not account for more than 25% of the oligonucleotide sequence. The non-complementary regions might be single-stranded overhangs on either side of the double stranded oligonucleotide; loop regions of a hairpin structure or mismatches within the double stranded sequence.

Single stranded oligonucleotides comprise one continuous stretch of nucleotides. Double stranded oligonucleotides do comprise either (i) an oligonucleotide having a continuous backbone forming a hairpin structure, (ii) two oligonucleotides having a sequence that is essentially complementary to each other. Structures (i) or (ii) may have a single strand break, as it is the case with (iii) a first oligonucleotide having a continuous backbone in combination with a two parts of a second oligonucleotide having a sequence that is essentially complementary to the first one, the resulting structure thus having three oligonucleotides forming a double stranded sequence or (iv) a first oligonucleotide forming an incomplete hairpin in combination with a second, shorter oligonucleotide essentially completing the hairpin.

It is an object of this invention to provide oligonucleotides having improved properties such as higher potency or better specificity. The oligonucleotides of this invention can feature an improved import of oligonucleotides into cells, which means the uptake from an extracellular space into the cytosol or nucleus or other intracellular compartments of cells, preferably eukaryotic cells. The invention is limited to the structure and size of the oligonucleotides defined above, but is agnostic to the intracellular mode of action of an oligonucleotide.

Since the mode of action provides popular means to categorize oligonucleotides, a non-limiting list of single-stranded oligonucleotides includes: antisense oligonucleotides, anti-miR or antagomir oligonucleotides, translation inhibitors, oligonucleotides for alternative splicing, DNAi oligonucleotides, single-stranded siRNA, decoy oligonucleotides for triplett repeats, guide strands for gene editing enzymes and others. A non-limiting list of double stranded oligonucleotides includes: siRNA, miRNA, dicer substrates, decoy oligonucleotides, saRNA, DNAzymes, RNAzymes, immunostimulatory dsRNA and others.

Elements Used for the Construction of Oligonucleotides

Internucleoside Linkages

The oligonucleotides of this invention have internucleoside linkages that comprise a phosphorus atom. Specifically, the internucleoside linkage can be a phosphodiester, a phosphorothioate (sometimes referred to as phosphothioate) or a phosphotriester. The internucleoside linkages of an oligonucleotide may be exclusively phosphodiester, exclusively phosphorothioate, or exclusively phosphotriester linkages. In a further embodiment, these types of linkages may be combined within a given oligonucleotide, preferably in combinations of phosphorothioate with phosphodiester internucleoside linkages.

Oligonucleotides having a peptide backbone (the PNA's) or those using morpholine as an internucleoside linkage are not within the scope of this invention.

Nucleobase

The oligonucleotides of this invention may have any type of nucleobases. With preference, nucleobases are selected from the group of adenine, guanine, thymine, cytosine, uracile (resulting in uridine or pseudouridine), 5'-methylcytosine, 5-hydroxymethylcytosine, dihydrouracil, xanthine, hypoxanthine or 7-methylguanine or derivatives of the aforementioned nucleobases within the sequence. It is further possible to include abasic sites (monomeric units) within the sequence, so that such abasic sites account for no more than 10% of the sequence length. If the oligonucleotide of the invention comprises abasic monomeric units, these monomeric units are also counted as nucleotides when determining the length or number of nucleotide units of the oligonucleotide. Preferably, however, all sugar moieties of the oligonucleotides of the invention carry a nucleobase.

Nucleoside Sugars

Furanoses, specifically ribose is the most widely used nucleoside sugar moiety. Substitutions in the 2' position of the furanose ring structure are widely used and popular modifications include 2'O-methyl, 2'methoxyethyl, 2' fluoro and the like.

Recently, the class of 2'4' bridged nucleoside sugars has received specific attention as so-called locked nucleic acids (LNA). Nucleotide analogues with constrained North type (N-type; C3'-endo type) furanose ring conformations mediate strong binding toward an RNA target, with LNA being a prominent example. An LNA monomer contains an O2'-C4' methylene linkage that locks the furanose ring in an N-type conformation leading to unprecedented binding affinity toward complementary RNA for antisense oligonucleotides (ASOs) composed of a mixture of e.g. LNA and DNA nucleotides [Koshkin, A. A.; Singh, S. K.; Nielsen, P.; Rajwanshi, V. K.; Kumar, R.; Meldgaard, M.; Olsen, C. E.; Wengel, J. *Tetrahedron* 1998, 54, 3607-3630; Obika, S.; Nanbu, D.; Hari, Y.; Andoh, J.-i.; Mono, K.-i.; Doi, T.; Imanishi, T. *Tetrahedron Lett.* 1998, 39, 5401-5404; Petersen, M.; Wengel, J. *Trends Biotechnol.* 2003, 21, 74-81; Vester, B.; Wengel, J. *Biochemistry* 2004, 43, 13233-13241].

Incorporation of LNA nucleotides into an ASO induces formation of almost canonical A-form helix structures of the duplexes formed with RNA complements [Petersen, M.; Bondensgaard, K.; Wengel, J.; Jacobsen, J. P. *J. Am. Chem. Soc.* 2002, 124, 5974-5982; Nielsen, K. E.; Rasmussen, J.; Kumar, R.; Wengel, J.; Jacobsen, J. P.; Petersen, M. *Bioconjugate Chem.* 2004, 15, 449-457; Nielsen, C. B.; Singh, S. K.; Wengel, J.; Jacobsen, J. P. *J. Biomol. Struct. Dyn.* 1999, 17, 175-191; Nielsen, K. E.; Singh, S. K.; Wengel, J.; Jacobsen, J. P. *Bioconjugate Chem.* 2000, 11, 228-238], and LNA thus can be characterized as a structural mimic of RNA though it lacks the 2'-OH group of an RNA nucleotide.

Without being limited to ASO, LNA-nucleotide-containing oligonucleotides have likewise shown promising properties with respect to targeting microRNAs, i.e. as so-called antiMiRs, and one LNA oligonucleotide targeting microRNA 122 is currently in clinical phase 2 studies as a drug to treat HCV infection [www.santaris.com]. Furthermore, LNA-modified oligonucleotides have shown promise as splice-modulating compounds [B. Bestas et al., *J. Clin. Investigation,* 2014, 9, 4067], and also as so-called blockmirs which are single-stranded oligonucleotides which target the microRNA binding sites [www.mirrx.dk].

A number of other locked nucleotides, i.e. analogs of LNA nucleotides, such as BNAs, carbocyclic-LNAs and CEt have been studied in the context of therapeutic oligonucleotides [Rahman, S. M. A et al., *Chem. Lett.* 2009, 38, 512] [Zhou, C. and Chattopadhyaya, J., *Curr. Opin. Drug Disc. Devel.,* 2009, 12, 2180] [Seth, P. P. and Swayze, E. E., in Natural Products in Medicinal Chemistry, Ed. Hanessian, S, Wiley-VCH, Weinheim, 1$^{st}$ ed., 2014, 203-439].

Amongst the locked nucleotides, the 2'-amino LNA nucleotides are of particular interest [U.S. Pat. No. 7,569, 575 to Soerensen et al.] but have seen little development by today. Oligonucleotides comprising 2' amino LNA share the improved binding of other ASO comprising N-type nucleotides but in addition, their 2' nitrogen provides an easily accessible site for chemical substitution. The modifications on the 2' position may comprise alkylations or acylations and a few acyl-amino-LNA such as palmitoyl-amino-LNA and 2' amino-LNA conjugated to polyaromatic dyes are known as monomers and oligomers, as recently reviewed [I. K. Astakhova and J. Wengel, Acc. Chem. Res., 2014, 47, 1768]. When compared to the corresponding DNA/RNA oligonucleotides, these modified amino-LNA oligonucleotides generally display increased affinity towards complementary DNA/RNA strands much in line with the increased affinity observed for the corresponding LNA oligonucleotides.

Glycyl-amino-LNA- and palmitoyl-amino-LNA monomers can be mixed with LNA and DNA monomers [Johannsen, M. W. et al., Org. Biomol. Chem., 2011, 9, 243]. Nucleotide monomers composed of pyrene linked to amino-LNA monomers via an N2'-linker have been reported to be useful as fluorescent probes, and acyl-amino-LNA derivatives containing various amino acids as acyl group have been shown to be compatible (mixable in the same strand or oligonucleotide) with DNA nucleotides, and 2'-amino-LNA and 2'-N-methyl-amino LNA monomers have been shown to be useful in gapmer antisense oligonucleotides [see I. K. Astakhova and J. Wengel, *Acc. Chem. Res.,* 2014, 47, 1768 and references cited therein].

It has also been reported that oligonucleotides containing a piperazino-modified 2'-amino-LNA monomer exhibit high duplex stability and remarkable nuclease resistance and did even succeed that of the parent amino-LNA [Lou, C., Vester, B. and Wengel, *J. Chem. Comm.* 2015. 19, 4024-4027] and extended towards the 3'-end of the oligonucleotide several DNA nucleotides away from the piperazino-modified 2'-amino-LNA monomer.

No reports, however, have been published on the use, potency or specificity of modified amino-LNA, e.g. glycyl- or palmitoyl-amino-LNA-containing oligonucleotides in the context of living cells, for improved cellular uptake of RNA, e.g. in the context of antisense, antimir or blockmir, or as compounds able to modulate splicing events.

Architecture of Certain Oligonucleotides

The efficiency of ASO containing modified nucleotides is often limited by their inability to induce degradation of target mRNA by the ubiquitous RNase H enzyme. Specifically, RNase H is incompatible with substrate duplexes with N-type nucleotides like LNA or O2'-alkylated-RNA nucleotides dispersed throughout the ASO [Sørensen, M. D.; Kvaerno, L.; Bryld, T.; Hakansson, A. E.; Verbeure, B.; Gaubert, G.; Herdewijn, P.; Wengel, J. *J. Am. Chem. Soc.* 2002, 124, 2164-2176; Lima, W. F.; Nichols, J. G.; Wu, H.; Prakash, T. P.; Migawa, M. T.; Wyrzykiewicz, T. K.; Bhat, B.; Crooke, S. T. *J. Biol. Chem.* 2004, 279, 36317-36326]. Such 02'-alkylated-RNA nucleotides can for example be 2'-O-methyl-RNA nucleotides or 2'-O-methoxyethyl-RNA (2'-MOE-RNA) nucleotides. This incompatibility has led to the gapmer architecture, wherein the N-type nucleotides are located at the 3' and 5' regions of the ASO, flanking a central core of DNA. The gapmer design thereby combines the high-affinity binding of the N-type nucleotides with a central strand of DNA supporting the catalytic activity of RNAseH [U.S. Pat. No. 6,107,094 to Crooke, S.].

For antisense applications, the gapmer architecture is frequently used. Gapmers are chimeric ASOs having a central continuous stretch of RNase H recruiting nucleotides (typically DNA or phosphorothioate DNA nucleotides but alternatively e.g. phosphorothioate FANA nucleotides [Lok, C. N.; Viazovkina, E.; Min, K. L.; Nagy, E.; Wilds, C. J.; Damha, M. J.; Parniak, M. A. Biochemistry 2002, 41, 3457-3467]) flanked by affinity-enhancing modified nucleotides (e.g. LNA, α-L-LNA or O2'-alkylated or O2' alkoxy-alkylated RNA nucleotides such 2' methoxyethyl RNA) [Jepsen, J. S.; Sorensen, M. D.; Wengel, J. *Oligonucleotides* 2004, 14, 130-146; Monia, B. P.; Lesnik, E. A.; Gonzalez, C.; Lima, W. F.; McGee, D.; Guinosso, C. J.; Kawasaki, A. M.; Cook, P. D.; Freier, S. M. *J. Biol. Chem.* 1993, 268, 14514-14522; Kurreck, J.; Wyszko, E.; Gillen, C.; Erdmann, V. A. *Nucleic Acids Res.* 2002, 30, 1911-1918; Frieden, M.; Christensen, S. M.; Mikkelsen, N. D.; Rosenbohm, C.; Thrue, C. A.; Westergaard, M.; Hansen, H. F.; Orum, H.; Koch, T. *Nucleic Acids Res.* 2003, 31, 6365-6372]. It has been found that the optimal gap size is motif-dependent, that a right balance between gap size and affinity is required [Kurreck, J.; Wyszko, E.; Gillen, C.; Erdmann, V. A. *Nucleic Acids Res.* 2002, 30, 1911-1918], and that the presence of one or two DNA-mimicking α-L-LNA monomers within the gap is compatible, at least in part, with RNase H activity [Sørensen, M. D.; Kvaerno, L.; Bryld, T.; Hakansson, A. E.; Verbeure, B.; Gaubert, G.; Herdewijn, P.; Wengel, J. *J. Am. Chem. Soc.* 2002, 124, 2164-2176; Frieden, M.; Christensen, S. M.; Mikkelsen, N. D.; Rosenbohm, C.; Thrue, C. A.; Westergaard, M.; Hansen, H. F.; Orum, H.; Koch, T. *Nucleic Acids Res.* 2003, 31, 6365-6372].

LNA and the gapmer architecture address potency and stability of an oligo, but do not provide any means for the cellular uptake.

Chemically modified nucleic acids having a reduced polarity in combination with pH-sensitivity have been described in [WO 08/074488 and WO2010004054, both to Panzner], thereby addressing the problem of membrane translocation. However, Panzner is silent on the potency and specificity of such modified nucleic acids.

The prior art is silent to the use of LNA nucleotides and in particular on the use of 2'-amino LNA nucleotides for the construction of TEE-modified nucleotides or zwitterionic nucleotides. The prior art is consequently silent with respect to the use of TEE-modified or zwitterionic nucleotides for the construction of oligonucleotides. The prior art teaches a difference in the hydrophobic, yet pH-sensitive TEE's and hydrophobic, but not pH-sensitive modifications such as alkylations or acylations.

It is an object of the invention to provide an oligonucleotide having improved efficacy and/or specificity, e.g. when used as ASO. It was surprising to find that TEE-modified (e.g. carboxyalkylated 2' amino LNA nucleotide units or carboxyalkylated 2' amido LNA nucleotides) contribute substantial potency and specificity to an oligonucleotide. It was further surprising to find that such improvements were observed also in the context of alkylated oligonucleotides. The carboxylated nucleotides of this invention therefore are important building blocks for the improvement of oligonucleotides.

BRIEF DESCRIPTION OF THE INVENTION

The invention discloses novel carboxylated (e.g. carboxyalkylated and/or carboxyarylated) 2'-amino LNA nucleotide derivatives and methods for obtaining such compounds. The invention further discloses novel alkylated or arylated 2' amino LNA nucleotide derivatives. The invention discloses the use of said 2' amino LNA derivatives for the construction of oligonucleotides and methods of obtaining the same.

More specifically, the invention provides the following subject-matters:
1) An oligonucleotide comprising from 3 to 100 nucleotide units, comprising one or more carboxylated 2'-amino-LNA nucleotide units of the following general formula (1')

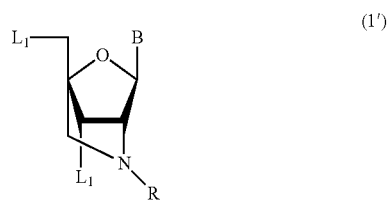

wherein
B is a nucleobase,
each of L1 is, independently from the other L1, an internucleoside linkage, a bond to a neighboring nucleotide unit or a terminal moiety selected from the group consisting of —OH, phosphate or a linker for the conjugation of the oligonucleotide to another molecule, and
R is a carboxylated substituent comprising one or two, preferably one, carboxyl group(s) and wherein R comprises from 6 to 40 carbon atoms and optionally from 1 to 3 further heteroatoms selected from O, N, and S (i.e. 1 to 3 heteroatoms other than oxygen atoms present in said carboxyl groups). The skilled person understands that there is generally one internucleoside linkage per nucleotide unit in an oligonucleotide.
2) The oligonucleotide according to item 1), wherein said oligonucleotide comprises from 5 to 50 nucleotide units and is double stranded or from 10 to 30 nucleotide units and is single stranded.
3) The oligonucleotide according to item 1) or 2), wherein R has from 6 to 20, preferably from 8 to 16 carbon atoms.
4) The oligonucleotide according to any one of items 1) to 3), wherein said carboxylated substituent is a carboxyhydrocarbyl group or a carboxyheterohydrocarbyl group, the heterohydrocarbyl moiety of which comprises from 1 to 3 heteroatoms selected from O, N, and S.
5) The oligonucleotide according to any one of items 1) to 4), wherein said carboxylated substituent is a carboxyalkyl or a carboxyaryl substituent.
6) The oligonucleotide according to any one of items 1) to 5), wherein the internucleoside linkage(s) is(are) selected from phosphodiester, phosphorothioate and/or phosphotriester linkages.
7) The oligonucleotide according to any one of items 1) to 6), wherein less than 40%, preferably less than 30%, more preferably less than 20% of the total number of nucleotide units in the oligonucleotide are carboxylated 2'-amino LNA nucleotide units of the general formulas (1') or (1") or (1''') below.
8) The oligonucleotide according to any one of items 1) to 6), wherein said oligonucleotide contains at most 8, preferably at most 6, more preferably at most 4, even more preferably at most 3 or even more preferably 2 of said carboxylated 2'-amino LNA nucleotide units of the general formulas (1'), or (1") or (1''') below.
9) The oligonucleotide according to any one of items 1) to 8), wherein said oligonucleotide has, from the 5'-end to the 3'-end, three segments: a 5'-end segment of at least 2 nucleotide units, a central binding segment of at least 6 nucleotide units in length, and a 3'-end segment of at least 2 nucleotide units in length, and
wherein said oligonucleotide contains at least two, preferably two, carboxylated 2'-amino-LNA nucleotide units in either the 5'-end segment or the 3'-end segment but none in the central segment; or contains at least one, preferably one, carboxylated 2'-amino-LNA nucleotide unit in each of said end segments, but none in the central segment.

10) The oligonucleotide according to any one of items 1) to 9), comprising 0, 1 or more hydrophobic nucleotide units that are independently selected from the group consisting of 2' amino LNA nucleotide moieties carrying on said 2'-amino group a (hetero)hydrocarbyl substituent, preferably a hydrocarbyl substituent, comprising from 8 to 40 carbon atoms and optionally from 1 to 3 heteroatoms selected from 0, N, and S; 2'-N—$C_3$-$C_7$-alkyl-amino-LNA nucleotide moieties; 2'-N—$C_3$-$C_7$-alkyl-amido-LNA nucleotide moieties; 2'-O—$C_3$-$C_{26}$-alkyl-RNA nucleotide moieties; 2'-O—$C_6$-$C_{26}$-aryl-RNA nucleotide moieties, 2'-O—$C_1$-$C_6$-alkyloxy-$C_3$-$C_{26}$-alkyl-RNA nucleotide moieties; and 2'-O—$C_1$-$C_6$-alkyloxy-$C_6$-$C_{26}$-aryl-RNA nucleotide moieties.

11) The oligonucleotide according to item 10), wherein less than 30%, preferably less than 20% of the total number of nucleotide monomer units in the oligonucleotide are hydrophobic nucleotide units as defined in item 10).

12) The oligonucleotide according to claim 15, wherein the carboxylated 2'-amino LNA nucleotide unit of formula (1') has, within the oligonucleotide, the following formula (1") or (1'''):

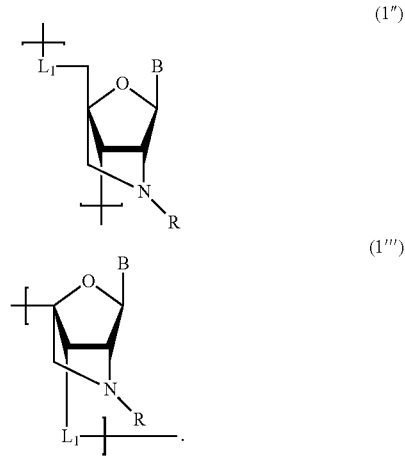

13) A method of transfecting cells with the oligonucleotide as defined in any one of items 1) to 12), comprising mixing said oligonucleotide with an aqueous buffer and treating said cells with the mixture obtained in the previous step.

14) A method of treating a human or animal by therapy, comprising administering the oligonucleotide as defined in any one of items 1) to 12) in a suitable carrier to an animal or human.

Further provided are the subject-matters of claims 1 to 14. Preferred embodiments are described in the description.

DETAILED DESCRIPTION OF THE INVENTION

Carboxylated such as Carboxyalkylated or Carboxyarylated 2' Amino LNA Nucleotides and Oligonucleotides Containing Same Generally, "carboxylated 2' Amino LNA" means that the 2'-amino group of the 2' amino LNA has a carboxylated substituent.

The secondary 2' amine of an amino LNA provides a preferred attachment site for derivatizations of the nucleotide. The resulting nucleotide of the invention has the following structure (1),

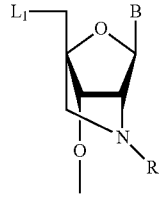

Structure (1)

wherein B is a nucleobase, L1 is an internucleoside linkage or absent and R is a carboxylated substituent comprising one or two carboxyl groups and wherein R is comprising from 6 to 40 carbon atoms and optionally from 1 to 3 heteroatoms selected from O, N, and S.

Structures (1), (1'), (1") and (1''') of the oligonucleotide of the invention are as defined above and as further explained in the following.

For clarity, the oxygen atoms forming the one or two carboxyl groups of R are not considered heteroatoms herein.

The nucleobase B can be any nucleobase and some preferred nucleobases can be selected from the group of adenine, guanine, thymine, cytosine, uracil (resulting in uridine or pseudouridine), 5'-methylcytosine, 5-hydroxymethylcytosine, dihydrouracil, xanthine, hypoxanthine or 7-methylguanine.

The internucleoside linkages are selected from phosphodiester, phosphorothioate or phosphotriester.

The carboxylated substituent R is comprising between 6 to 40 carbon atoms and preferred carboxylated substituents have between 6 to 20 carbon atoms, further preferred are carboxylated substituents having 8 to 16 carbon atoms.

The carboxyl group of the carboxylated substituent is the anionic carboxylate group of formula —COO— or its protonated form —COOH. In line with the general understanding of the skilled person, ester groups or amide groups are not carboxyl groups.

The carboxylated substituent R may be a carboxyhydrocarbyl group, or may be a carboxyheterohydrocarbyl group comprising from 1 to 3 heteroatoms selected from O, N, and S. The number of heteroatoms is preferably 1 or 2, and/or the type of heteroatoms are preferably O and N, most preferably O.

Where the carboxylated substituents are carboxyhydrocarbyl groups, the hydrocarbyl moieties of said carboxyhydrocarbyl groups may be saturated aliphatic hydrocarbyl moieties, unsaturated aliphatic hydrocarbyl moieties, alicyclic (saturated or unsaturated) hydrocarbyl moieties, aromatic hydrocarbyl moieties, or moieties comprising two or more moieties from the aforementioned list.

Examples of the carboxyhydrocarbyl group are carboxyalkyl, carboxyalkenyl, carboxyalkynyl, carboxycycloalkyl, carboxycycloalkenyl, carboxyalkylcycloalkyl, carboxyaryl, carboxyalkylaryl, carboxyarylalkyl and carboxyalkylarylalkyl groups. A carboxyalkylcycloalkylalkyl group is a further possibility.

It is possible to replace 1, 2 or 3, preferably 1 or 2, of the carbon atoms of the hydrocarbyl moieties of the carboxylated substituents by oxygen, nitrogen or sulfur, thereby forming carboxyheterohydrocarbyl moieties. It is understood that any such replacement by a heteroatom will include adjustment of bound hydrogen atoms to adjust to the valency of the exchanged heteroatom. In preferred embodiments, the heterohydrocarbyl moieties of the carboxyheterohydrocarbyl moieties comprise one or more functional group selected from —O—, —S—, —N(H)C(O)—, —C(O)

O—, —OC(O)N(H)—, —C(O)—, —C(O)—N(H)—, —N(H)—C(O)—O—, —O—C(O)—, or —S—S—. In some embodiments, the heterohydrocarbyl moieties contain a biradical of —NH—CH2-CH2-O— or —NH—CH2-CH2-C(O)O—, —NH—CH2-CH2-C(O)NH—, —NH—CH2-CH2-NH— or the N1,N4-piperazyl biradical.

In many embodiments, the heteroatoms of the carboxyheterohydrocarbyl moiety are located in the immediate vicinity to the 2' amino atom of the LNA, meaning that they are directly bound to the 2' amino atom. In preferred aspects they form the actual attachment site of said carboxyheterohydrocarbyl to the 2'-amino nitrogen of the 2'-amino-LNA unit. Such structures are generally known in the art as linker.

In aspects of the invention, the carboxylated substituent R and/or the hydrocarbyl moiety of the carboxyhydrocarbyl group is or comprises alkylene group(s) such as linear or branched alkylene group(s), and/or cycloalkylene group(s) such as $C_4$-$C_8$-cycloalkylene group(s); further possibilities are alkenylene, alkynylene, cycloalkenylene, alkylcycloalkylene, and alkylcycloalkylalkylene group(s).

Alkylene groups may be n-alkylene or isoalkylene groups. Examples of alkylene groups are methylene, ethylene, propylene, butylene, pentylene, hexylene, heptylene, octylene, nonylene, decylene, undecylene, dodecylene, tetradecylene or hexadecylene or octadecylene groups or constitution isomers thereof. Examples of cycloalkylene groups are cyclopentylene, cyclohexylene and cycloheptylene groups. Examples of alkylcycloalkylene groups are methylcyclopentylene, ethylcyclopentylene, propylcyclopentylene, butylcyclopentylene, pentylcyclopentylene, hexylcyclopentylene, methylcyclohexylene, ethylcyclohexylene, propylcyclohexylene, butylcyclohexylene, pentylcyclohexylene and hexylcylohexylene and constitution or stereoisomers thereof. One or more of these may be combined in a carboxylated substituent R or a hydrocarbyl moiety. Examples of alkenylene groups are ethenylene, propenylene, butenylene, pentenylene, hexenylene, heptenylene, octenylene, nonenylene, decenylene, undecenylene, dodecenylene, tetradecenylene or hexadecenylene or octadecenylene groups. Examples of alkynylene groups are ethynylene, propynylene, butynylene, pentynylene, hexynylene, or heptynylene groups. Examples of cycloalkenylene groups are $C_4$-$C_8$-cycloalkenylene groups such as cyclopentenylene, cyclohexenylene and cycloheptenylene groups. Examples of alkylcycloalkylalkylene groups are $C_1$-$C_6$-alkyl-$C_4$-$C_8$-cycloalkyl-$C_1$-$C_6$-alkylene groups.

The carboxylated substituents and/or the carboxyhydrocarbyl groups may be or may comprise carboxyalkyl or carboxycycloalkyl groups and may comprise from 6 to 20 carbon atoms. Such carboxylated substituents may be selected from the group consisting of carboxy-n-alkyl groups, branched carboxyalkyl groups or cyclic carboxyalkyl groups (i.e. carboxycycloalkyl groups). Other carboxylated substituents and/or carboxyhydrocarbyl groups are carboxyalkenyl, carboxyalkynyl, carboxyalkylcycloalkyl, and carboxyalkylcycloalkylalkyl groups and their constitution or conformation isomers. In a preferred embodiment, the carboxylated substituents and/or carboxyhydrocarbyl groups (such as carboxylalkyl groups) are radicals of acids selected from hexanoic acid, heptanoic acid, octanoic acid, nonanoic acid, decanoic acid, undecanoic acid, dodecanoic acid, tetradecanoic acid, hexadecanoic acid, octadecanoic acid, oleic acid, linoleic acid, 2-cyclohexylacetic acid, 4-cyclohexylbutyric acid, 6-cyclohexylhexanoic acid, 2-(2', 3' or 4' alkylcyclohexyl)-acetic acid or 4-(2', 3' or 4' alkylcyclohexyl)-butyric acid or 6-(2', 3' or 4' alkylcyclohexyl)-hexanoic acid, wherein said alkyl of the alkylcyclohexyl moiety may be an ethyl, propyl, butyl, pentyl, hexyl, heptyl, octyl, nonyl, decyl, undecyl or dodecyl group, preferably an hexyl, heptyl, octyl, nonyl or decyl group or a constitutional isomer thereof.

In another aspect of the invention, the carboxylated substituent R, specifically the (hetero)hydrocarbyl moiety of the carboxy(hetero)hydrocarbyl group, is or comprises arylene group(s) and may have from 6 to 20 carbon atoms. Aryl groups forming said arylene groups include aromatic hydrocarbyl groups (carbon-only aryl groups) and aromatic heterohydrocarbyl groups (heteroaryl groups), the former being preferred. Examples of the former are phenyl, naphthyl, anthracenyl and phenanthryl, whereby phenyl and naphthyl are preferred and phenyl is most preferred.

In another aspect of the invention, the carboxylated substituent R, specifically the hydrocarbyl moiety of the carboxyhydrocarbyl group comprise aryl groups such as in alkylaryl or arylalkyl or alkylarylalkyl groups, and examples of alkylaryl groups are methylphenyl (tolyl), ethylphenyl, 4-isopropylphenyl, and xylyl groups. Examples of arylalkyl (aralkyl) groups are benzyl, phenylethyl and trityl groups. Examples of alkylarylalkyl groups are o-, m- or p-methylbenzyl, o-, m- or p-ethylbenzyl, o-, m- or p-propylbenzyl, and the constitutional isomers of isopropylbenzyl, butylbenzyl, pentylbenzyl, hexalbenzyl, heptylbenzyl, octylbenzyl, nonylbenzyl, decylbenzyl, undecylbenzyl or dodecylbenzyl groups.

Examples of carboxyaryl groups are benzoic and naphthoic acid groups. Examples of carboxyalkylaryl groups are phenylacetic acid and cinnamic acid groups.

Carboxyarylalkyl moieties may for example be selected from the group of radicals comprising o-, m- or p-alkyl benzoic acid wherein the alkyl group is a methyl, ethyl, propyl, butyl, pentyl, hexyl, heptyl, octyl, nonyl, decyl, undecyl or dodecyl group.

Carboxyalkylarylalkyl moieties may for example be selected from the group of radicals comprising o-, m- or p-alkyl phenylacetic or cinnamic acid wherein the alkyl group is a methyl, ethyl, propyl, butyl, pentyl, hexyl, heptyl, octyl, nonyl, decyl, undecyl or dodecyl group.

In one embodiment, the heterohydrocarbyl and carboxyheterohydrocarbyl groups differ from the hydrocarbyl and carboxyhydrocarbyl groups defined above, respectively, in that the former contain from 1 to 3 heteroatoms selected from O, N and S (preferred heteroatoms and numbers of heteroatoms as defined above).

In aspects of the invention, the carboxy(hetero)hydrocarbyl group can be a carboxyaryloxyalkyl moiety, for example the selected form the group of radicals comprising o-, m- or p-alkoxy-benzoic acid wherein the alkoxy group is a methoxy, ethoxy, propyloxy, butyloxy, pentyloxy, hexyloxy, heptyloxy, octyloxy, nonyloxy, decyloxy, undecyloxy or dodecyloxy group or a constitutional isomer of said alkoxy groups and wherein the alkyl group is bound to the aryl group through an oxygen atom as shown in structure (7).

In other aspects of the invention, the carboxy(hetero) hydrocarbyl group can be a carboxyalkylaryloxyalkyl moiety, for example the selected form the group of radicals comprising o-, m- or p-alkoxy-phenylacetic or cinnamic acid wherein the alkoxy group is a methoxy, ethoxy, propyloxy, butyloxy, pentyloxy, hexyloxy, heptyloxy, octyloxy, nonyloxy, decyloxy, undecyloxy or dodecyloxy group or a constitutional isomer of said alkoxy groups and wherein the alkyl group is bound to the aryl group through an oxygen atom as shown in structure (7).

Specific carboxylated 2' amino LNA units may be selected from the structures (2) to (7) listed in table 1, wherein B and L1 are defined as above and Y is oxygen or absent, the latter describing the occurrence of a methylene group at this position.

TABLE 1 specific carboxylated 2' amino LNA

| | | |
|---|---|---|
| (2) | 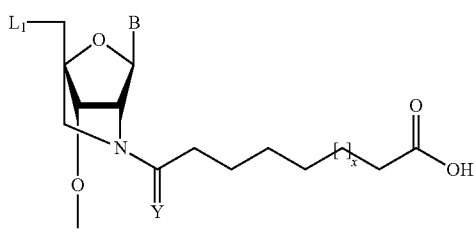 | R is a carboxyhydrocarbyl (Y = absent) or carboxyheterohydrocarbyl (Y = oxygen), wherein x is 1, 2, 3, 4, 5, 7, 9 or 11 |
| (3) | 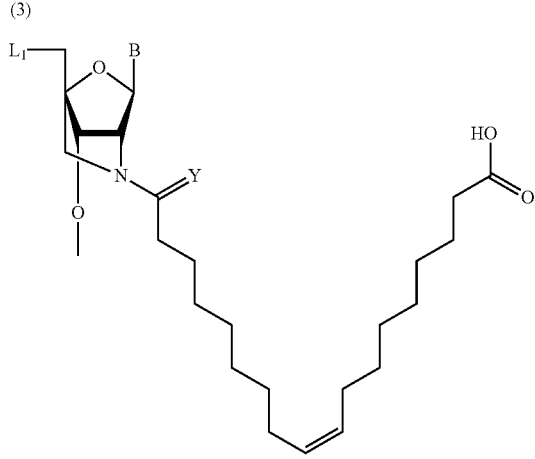 | R is a carboxyhydrocarbyl (Y = absent) or carboxyheterohydrocarbyl (Y = oxygen) wherein the hydrocarbyl moiety is derived from oleic acid. |
| (4) | 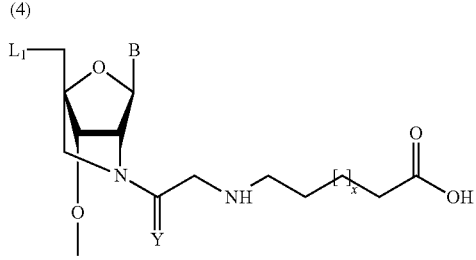 | R is a carboxyheterohydrocarbyl, Y can be oxygen or absent and x is 4, 5, 6, 7, 8, 10, 12 or 14 |
| (5) | 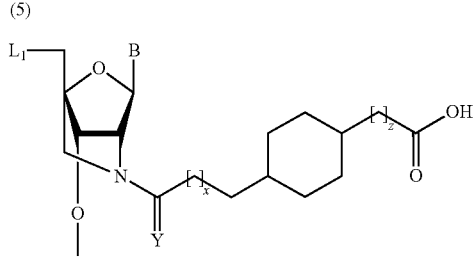 | R is a carboxyhydrocarbyl (Y = absent) or carboxyheterohydrocarbyl (Y = oxygen), wherein x is 1, 2, 3, 4, 5, 6, 7, 8, 9 or 11 and z is 0, 1, 2, 3 or 4 and x + z is between 5 and 12 |
| (6) | 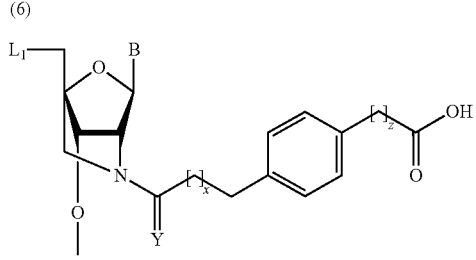 | R is a carboxyhydrocarbyl (Y = absent) or carboxyheterohydrocarbyl (Y = oxygen), wherein x is 1, 2, 3, 4, 5, 6, 7, 8, 9 or 11 and z is 0, 1, 2, 3 or 4 and x + z is between 5 and 12 |

TABLE 1-continued specific carboxylated 2' amino LNA (7) [structure shown] R is a carboxyhydrocarbyl (Y = absent) or carboxyheterohydrocarbyl (Y = oxygen), wherein x is 1, 2, 3, 4, 5, 6, 7, 8, 9 or 10 and z is 0, 1, 2, 3 or 4 and x + z is between 5 and 13

The carboxylated substituent generally has a region that is proximal and another region that is distal to the 2' nitrogen atom of the 2'-amino-LNA. The proximal region is the portion of the carboxylated substituent close to the 2'-amino nitrogen atom of the LNA. It does comprise the attachment site of R to the 2' amino LNA, specifically the carbon atom directly bound to the 2' nitrogen of the LNA and the adjacent carbon atoms of R wherein the number of adjacent carbon atoms can be 4, 3, 2, 1 or 0. The distal region is the outermost portion of the carboxylated substituent when starting from the 2' nitrogen atom of the LNA. It does comprise the outermost carbon atom and the adjacent carbon atoms of R wherein the number of adjacent carbon atoms can be 4, 3, 2, 1 or 0.

Preferably, the carboxylic acid moiety of the substituent is located in the distal portion of R. In many embodiments the carboxylic acid group is located at the terminal position of R which is the outermost position of R relative to the attachment site of R at the 2' amino LNA.

The carboxylated substituent R may be grafted onto the 2' amino group of the 2'-amino-LNA directly. In preferred embodiments of this invention, R is coupled to the 2' amino group to form a carbon-nitrogen single bond and a tertiary 2'-amine or forms, together with a carbonyl group of R, an amide group as shown in the structures (2) to (7).
In other embodiments, R is bound to the 2' amino group through a functional group comprising the heteroatoms of R, such as —N(H)C(O)—, —N(H)—C(O)—O—, —NH—CH2-CH2-O— or —NH—CH2-CH2-C(O)O—, —NH—CH2-CH2-C(O)NH—, NH—CH2-CH2-NH— or through the N1,N4-piperazyl biradical. These functional groups are part of R.

Since the nucleotide monomer units are linked to form the oligonucleotide of the invention, the term "nucleotide monomer unit" or, briefly, "monomer unit" indicates that the nucleotide monomer is not an isolated molecule, but a chemical moiety linked to one (in case of the terminal nucleotides) or two other nucleotide monomer units in the oligonucleotide. The term "oligonucleotide" is sometimes abbreviated as "oligo" herein.

(Hetero)hydrocarbyl-2' Amino LNA Nucleotides such as Alkylated or Arylated 2' Amino LNA Nucleotides The invention also provides oligonucleotides comprising, additionally, certain hydrophobic substituents on the 2'-amino group of 2'-amino-LNA nucleotide units, such as alkylated or arylated 2'-amino-LNA nucleotide units. The general form of alkylated or arylated 2' amino LNA nucleotides has been included into U.S. Pat. No. 6,670,461 [to Wengel and Nielsen], but the '461 patent is silent with regard to specific alkylated or arylated 2' amino LNA nucleotides.

Some alkylated and acylated 2' amino LNA have also been described in [I. K. Astakhova and J. Wengel, Acc. Chem. Res., 2014, 47, 1768] and in [Sørensen, M. D.; Petersen, M.; Wengel, J., Chem. Commun. 2003, 17, 2130-2131.], specifically a palmitoylated 2' amino LNA and a conjugates to polyaromatic hydrocarbon dyes. Conjugates to polyaromatic dyes are used for labelling purposes and are not considered part of this invention. Also, the single known acylated compound of palmitoylated 2' amino LNA is excluded from the group of novel alkylated or arylated 2' amino LNA nucleotides disclosed here.

The hydrophobic, e.g. alkylated or arylated, 2'-amino-LNA nucleotide units have the general structure (10),

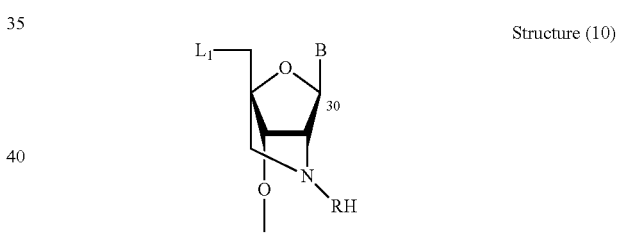

Structure (10)

wherein B is a nucleobase, L1 is an internucleoside linkage or absent and RH is a hydrophobic moiety comprising from 8 to 40 carbon atoms and optionally from 1 to 3 heteroatoms selected from O, N, and S.

RH may exclude a palmitoyl residue bound as an amide to the 2' amino LNA and RH may not comprise polyaromatic hydrocarbons or heterocarbons having a conjugated system comprising more than 10 atoms and being linked by alternating saturated and unsaturated bonds.

The hydrophobic substituent RH is comprising between 8 to 40 carbon atoms and preferred hydrophobic substituents have between 8 to 20 carbon atoms, further preferred are substituents having 8 to 16 carbon atoms.

Thus, the hydrophobic substituent RH may be a hydrocarbyl group as defined (except for the carbon atom numbers) above or may be a heterohydrocarbyl group comprising from 1 to 3 heteroatoms selected from O, N, and S as defined (except for the carbon atom numbers) above. However, the number of heteroatoms of the heterohydrocarbyl group is preferably 1 or 2, more preferably 1, and/or the heteroatoms are preferably O and N, more preferably O. Otherwise, the definitions given above for the hydrocarbyl moiety of the carboxyhydrocarbyl group also apply to the hydrocarbyl group of the hydrophobic substituent; and the definitions given above for the heterohydrocarbyl moiety of the carboxyheterohydrocarbyl group also apply to the heterohydrocarbyl group of the hydrophobic substituent.

The hydrocarbyl moieties may be saturated aliphatic hydrocarbyl moieties, unsaturated aliphatic hydrocarbyl moieties, alicyclic hydrocarbyl moieties, aromatic hydrocarbyl moieties, or moieties comprising two or more moieties from the aforementioned list.

Examples of the hydrocarbyls are alkyl, alkenyl, alkynyl, cycloalkyl, cycloalkenyl, alkylcycloalkyl, cycloalkyl, alkylcycloalkyl, aryl, alkylaryl, arylalkyl and alkylarylalkyl groups comprising between 8 and 40 carbon atoms.

It is possible to replace 1, 2 or 3, preferably 1 or 2, of the carbon atoms of the hydrocarbyl moieties of the hydrophobic substituents by oxygen, nitrogen or sulfur, thereby forming heterohydrocarbyl moieties. It is understood that any such replacement by a heteroatom will include adjustment of bound hydrogen atoms to adjust to the valency of the exchanged heteroatom. In preferred embodiments, the heterohydrocarbyl moieties comprise one or more functional group selected from —O—, —S—, —N(H)C(O)—, —C(O)O—, —OC(O)N(H)—, —C(O)—, —C(O)—N(H)—, —N(H)—C(O)—O—, —O—C(O)—, or —S—S—. In some embodiments, the heteroatoms form a biradical of —NH—CH2-CH2-O— or —NH—CH2-CH2-C(O)O—, —NH—CH2-CH2-C(O)NH— or the N1,N4-piperazyl biradical.

In aspects of the invention, the hydrophobic substituent RH is a linear or branched alkyl or alkylcycloalkyl group having between 8 and 40, preferably between 8 and 16 carbo atoms and is linked to the 2' amino group of the LNA either directly or as an amide. Alkyl groups may be n-alkyl or isoalkyl groups. Examples of alkyl groups are octyl, nonyl, decyl, undecyl, dodecyl, tetradecyl or hexadecyl or octadecyl groups or constitution isomers thereof. Specific examples of alkyl groups are oleyl or lineyl groups.

Examples of alkylcycloalkyl groups are propylcyclopentyl, butylcyclopentyl, pentylcyclopentyl, hexylcylopentyl, heptylcyclopentyl, octylcyclopentyl, nonylcyclopentyl, decylcyclopentyl, undecylcyclopentyl and dodecylcyclopentyl groups, as well as ethylcyclohexyl, propylcyclohexyl, butylcyclohexyl, hexylcyclohexyl, hexylcylohexyl, heptylcyclohexyl, octylcyclohexyl, nonylcyclohexyl, decylcyclohexyl, undecylcyclohexyl and dodecylcyclohexyl groups and constitution or stereoisomers thereof. Specific examples of alkylcycloalkyl groups are steryl groups such as cholesteryl groups or tocopheryl or carotinoyl groups.

In another aspect of the invention, the hydrophobic substituents RH do comprise one or more aryl or arylene groups and have from 8 to 40 carbon atoms, preferably between 8 and 16 carbon atoms and are linked to the 2' amino group of the LNA either directly or as an amide.

Aryl groups or the aryl groups forming said arylene groups include aromatic hydrocarbyl groups (carbon-only aryl groups) and aromatic heterohydrocarbyl groups (heteroaryl groups). Examples of the former are phenyl, biphenyl, naphthyl or xylyl groups. Nitrogen-containing heteroaryl groups preferably shall have a pK value of <6 for avoiding additional cationic charges at neutral pH. Examples of such nitrogen-containing heteroaryl groups are indolyl, pyridinyl, pyrazinyl, pyridazinyl, pyrimidinyl, cinnolinyl, phthalazinyl and purinyl groups. Oxygen-containing heterohydrocarbyl groups that form hydroxy groups preferably have a pK>12 for avoiding negative charges at neutral pH and examples of such oxygen containing groups are o-, m- or p-phenyl, resorcinyl, pyrogallyl or benzophenone groups.

The hydrocarbyl groups can also be alkylaryl or arylalkyl or alkylarylalkyl groups. Examples of alkylaryl groups are ethylphenyl, propylphenyl, isopropylphenyl, butylphenyl, pentylphenyl, hexylphenyl, heptylphenyl, octylphenyl, nonylphenyl, decylphenyl, undecylphenyl or dodecylphenyl groups.

Examples of arylalkyl (aralkyl) groups are benzyl, phenylethyl and trityl groups. Examples of alkylarylalkyl groups are o-, m- or p-ethylbenzyl, o-, m- or p-propylbenzyl, and the constitutional isomers of isopropylbenzyl, butylbenzyl, pentylbenzyl, hexylbenzyl, heptylbenzyl, octylbenzyl, nonylbenzyl, decylbenzyl, undecylbenzyl or dodecylbenzyl groups.

Aryloxyalkyl moieties as examples for heterohydrocarbyl groups may for example be phenylethers wherein the phenyl residue forms an ether with an ethyl, propyl, butyl, pentyl, hexyl, heptyl, octyl, nonyl, decyl, undecyl or dodecyl group or constitutional isomers of said groups.

Specific alkylated or acylated 2' amino LNA may be selected from the structures (11) to (16) listed in table 2, wherein B and L1 are defined as above and Y is oxygen or absent.

TABLE 2

Specific hydrophobic 2' amino LNA

| (11) | |
|---|---|
| 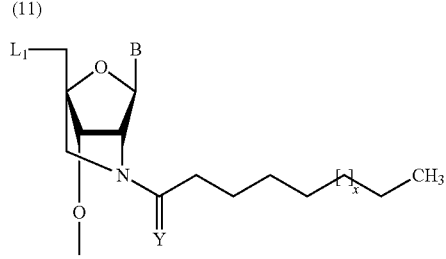 | RH is a hydrocarbyl (Y = absent) or heterohydrocarbyl (Y = oxygen), wherein x is 1, 2, 3, 4, 5, 7, 9, 11 or 13 |

TABLE 2-continued

Specific hydrophobic 2' amino LNA

(12) 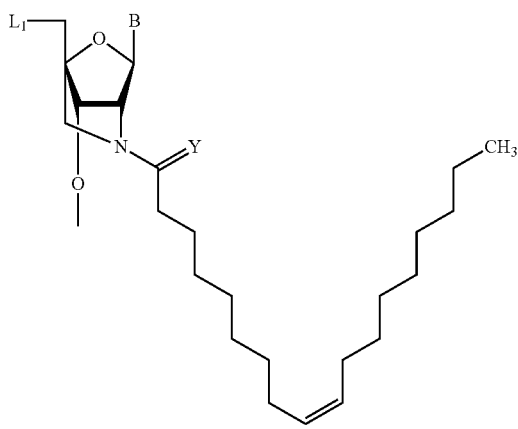

RH is a hydrocarbyl (Y = absent) or heterohydrocarbyl (Y = oxygen) wherein the hydrocarbyl moiety is an oleoyl residue.

(13) 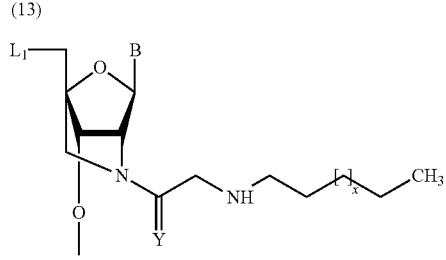

RH is a heterohydrocarbyl, Y can be oxygen or absent and x is 2, 3, 4, 5, 6, 7, 8, 10, 12 or 14

(14) 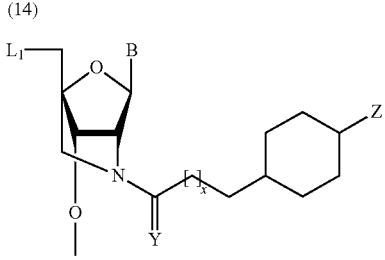

RH is a hydrocarbyl (Y = absent) or heterohydrocarbyl (Y = oxygen), wherein x is 1, 2, 3, 4, 5, 6, 7, 8, 9, 11 or 13 and Z is H or a methyl, ethyl, propyl, butyl, pentyl or hexyl group or a constitutional isomer thereof and the combined number of carbon atoms in x and Z is between 1 and 13, preferably between 5 and 9.

(15) 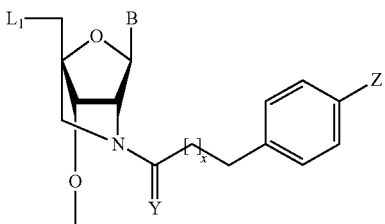

RH is a hydrocarbyl (Y = absent) or heterohydrocarbyl (Y = oxygen), wherein x is 1, 2, 3, 4, 5, 6, 7, 8, 9, 11 or 13 and Z is H or a methyl, ethyl, propyl, butyl, pentyl or hexyl group or a constitutional isomer thereof and the combined number of carbon atoms in x and Z is between 1 and 13, preferably between 5 and 9.

(16) 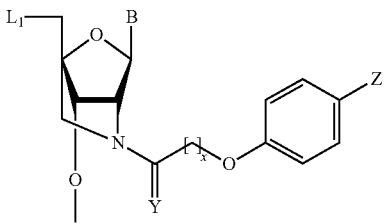

RH is a hydrocarbyl (Y = absent) or heterohydrocarbyl (Y = oxygen), wherein x is 1, 2, 3, 4, 5, 6, 7, 8, 9, 10 or 12 and Z is H or a methyl, ethyl, propyl, butyl, pentyl or hexyl group or a constitutional isomer thereof and the combined number of carbon atoms in x and Z is between 1 and 13, preferably between 6 and 10.

The hydrophobic substituent RH may be grafted onto the 2' amino group of the LNA directly. In preferred embodiments of this invention RH is coupled directly to the 2' amino group to form a tertiary 2'-amino group or an amide group together with a carbonyl group of RH, as shown in the structures (2) to (7).

In other embodiments RH is bound through a functional group comprising the heteroatoms of RH, such as —N(H)C(O)—, —N(H)—C(O)—O—, —NH—CH2-CH2-O— or —NH—CH2-CH2-C(O)O—, —NH—CH2-CH2-C(O)NH—, NH—CH2-CH2-NH— or through the N1,N4-piperazyl biradical. These functional groups are part of group RH.

Oligonucleotides Comprising (Hetero)Hydrocarbyl (Such as Carboxyalkylated or Carboxyarylated)-2' Amino LNA The invention provides oligonucleotides containing one or more of the carboxylated (such as carboxyalkylated and/or carboxyarylated)-2' amino LNA nucleotide units, e.g. carboxyalkyl- and/or carboxyaryl-2' amino LNA nucleotide units, of this invention together with other nucleotide monomers that can be DNA, RNA or chemically modified nucleotide monomers. The internucleoside linkages of said oligonucleotide are phosphodiester (also referred to herein as "PO") and/or phosphorothioate linkages (also referred to herein as "PS") or phosphotriester linkages.

In one aspect, the oligonucleotide of the invention has between 3 and 100 nucleotide units, wherein one or more of the carboxylated (included the carboxyalkylated or carboxyarylated) 2' amino LNA are present. In embodiments of said aspect, the oligonucleotide having between 3 and 100 nucleotides is essentially a single-stranded oligonucleotide. Preferred single-stranded oligonucleotides of the invention comprise at least 9, preferably at least 10 and more preferably at least 11 nucleotides (nucleotide units) and may comprise up to 30, preferably up to 26 and more preferably up to 20 nucleotides (nucleotide units). The oligonucleotide may consist of 10 to 30 nucleotides, preferably from 12 to 26 nucleotide monomer units, even more preferably from 14 to 24 monomer units, and even more preferably from 14 to 20 monomer units. In one embodiment, the oligonucleotide has from 12 to 16 nucleotide monomer units.

In other aspects of the invention, the oligonucleotides comprising carboxylated (such as carboxyalkylated or carboxyarylated) 2' amino LNA are double-stranded. Without being limited to a specific mode of action, such double-stranded oligonucleotides might be siRNA or miRNA. Preferably, the siRNA or miRNA oligonucleotides have a double stranded portion of at least 19 and less than 30 base pairs, more preferred between 21 and 27 base pairs. Since the nucleotide monomer units are linked to form the oligonucleotide, the term "nucleotide monomer unit" or, briefly, "monomer unit" indicates that the nucleotide monomer is not an isolated molecule, but a chemical moiety linked to one (in case of the terminal nucleotides) or two other nucleotide monomer units in the oligonucleotide.

In the oligo of the invention, the nucleotides of the oligonucleotide are linked by phosphodiester linkages and/or phosphorothioate linkages and/or phosphotriester linkages. A given oligonucleotide may have only one type of these linkages, two types of these, or even all three types of linkages. In preferred embodiments, in the single stranded oligonucleotide, at least 50%, preferably at least 70%, more preferably at least 80%, preferably at least 90%, and most preferably at least 95% of internucleoside linkages are phosphodiester linkages (PO), and remaining internucleoside linkages may be phosphorothioate linkages and/or phosphotriester linkages. In a preferred embodiment, the internucleoside linkages of the oligonucleotide of the present invention are all-PO (all-phosphodiester). There is also an embodiment with all-PS (all-phosphorothioate) or a mixture of PO and PS internucleoside linkages. These types of linkages as well as methods of automated synthesis of oligos having these linkages are known to the skilled person from general knowledge.

The nucleobase (briefly: "base") of the nucleotide monomer units are not particularly limited in the oligos of the invention; they may be the standard nucleobases adenine, guanine, cytosine, thymine and uracil, or any derivative thereof or any chemically modified nucleobase, with 5-methylcytosine and 5-substituted uracil being particularly preferred examples.

The oligonucleotide of the invention has one or more of the carboxylated (such as the carboxyalkylated or carboxyarylated) 2' amino LNA nucleotide units disclosed above. As with the other nucleotide monomers, the nucleobase of the carboxylated 2' amino LNA is not specifically limited and may be adenine, guanine, cytosine, thymine and uracil, or any derivative thereof or any chemically modified nucleobase. For ease of preparation of 2'-amino-LNA nucleosides, the base of the substituted 2'-amino-LNA moiety may be thymine or 5-methylcytosine.

The other nucleotide monomer units in the oligo of the invention are, with regard to their ribose moiety or its derivative, not specifically restricted. They may be DNA or RNA or may have chemically modified ribose derivatives. They may thus be DNA, RNA, LNA, BNA, UNA, 2'-amino-LNA, alkylated, acylated or arylated 2' amino-LNA, α-L-LNA, 2'-F-RNA, 2'-O-alkyl-RNA and/or 2'-O-alkoxyalkyl-RNA monomer units or mixtures thereof. 2'-O-Alkyl-RNA monomers may be 2'-O—$C_1$-$C_{26}$-alkyl-RNA monomer units. 2'-O-Alkyloxyalkyl-RNA monomer units may be 2'-O—$C_1$-$C_6$-alkyloxy-$C_1$-$C_{26}$-alkyl-RNA monomer units such as 2'-O-methoxyethyl-RNA units. Alkylated, acylated or arylated 2' amino-LNA have been described above in this invention and further include the palmitoylated 2' amino LNA described in [I. K. Astakhova and J. Wengel, *Acc. Chem. Res.*, 2014, 47, 1768].

BNA covers a number of locked nucleotides with bicyclic ribose units having a linker between the C2' and C4' atoms, including carbocyclic-LNAs and CEt [Rahman, S. M. A et al., *Chem. Lett.* 2009, 38, 512] [Zhou, C. and Chattopadhyaya, J., *Curr. Opin. Drug Disc. Devel.*, 2009, 12, 2180], and UNA is a class of nucleotide monomers having the ribose unit substituted by an acyclic unit, preferably a 2',3'-seco-RNA unit [Langkjr, N., Pasternak, A. and Wengel, J., *Bioorg. Med. Chem.* 2009, 17, 5420-5].

In a preferred embodiment, the oligo of the invention consists of the A, T/U, G, C ribo- or deoxyribonucleotide units or the chemically modified nucleotides mentioned before and one or more of the carboxylated 2'-amino LNA nucleotide units of the following general formula (1).

An example of other monomer units in the oligo of the invention are nucleotide monomer units chemically modified, preferably at the ribose moiety, with—e.g. antenna-like—mono-, di- or trimeric galactosyl or N-acetylamino galactosyl moieties. The invention includes, as a preferred embodiment, 3'-end or 5'-end conjugates of the oligonucleotides with such mono-, di- or trimeric galactosyl or N-acetylamino galactosyl moieties. The (e.g. antenna-like) mono-, di- or trimeric galactosyl or N-acetylamino galactosyl moieties may be linked to the 2'-amino group of amino- LNA nucleotide monomer units in an oligonucleotide. Recently, a number of reports have illustrated how targeted delivery of antisense oligonucleotides to the liver, e.g. to hepatocytes, has been achieved using conjugates of antisense oligonucleotides with (e.g. antenna-like) mono-, di- or trimeric galactosyl or N-acetylamino galactosyl moieties. These have been linked to the antisense oligonucleotide using a number of different linkages—both stable linkages or linkages which are cleaved in vivo—and general methods for their preparation are described in the following two references: [Prakash, T. P. et al., *Nucleic Acids Res.* 2014, 42, 8796-8807; Albæk, N. et al., US20150368642]. These methods can be used for design and synthesis of similar conjugation of the antisense oligonucleotides of this invention with antenna-like mono-, di- or trimeric galactosyl or N-acetylamino galactosyl moieties.

The number of carboxylated (e.g. carboxyalkylated or carboxyarylated) 2' amino LNA nucleotide monomer units in the oligo of the invention is at least one. Generally, not more than 40%, preferably not more than 30%, more preferably not more than 20% of the total number of monomer units in the oligo are carboxyalkylated or carboxyarylated 2' amino LNA nucleotide monomers. The number of carboxylated (e.g. carboxyalkylated or carboxyarylated) 2' amino LNA nucleotide monomers in the oligo may be from 1 to 8, preferably from 1 to 6, more preferably from 2 to 4.

In one aspect of the invention, the oligonucleotides having one or more carboxylated 2' amino LNA nucleotides further comprise one or more nucleotide monomers having a hydrophobic substituent at their 2' position (herein referred to as "hydrophobic monomers" or hydrophobic nucleotides"). Nucleotide monomers having a 2' hydrophobic substituent (hydrophobic nucleotides) can independently be selected from the novel alkylated or arylated 2' amino LNA nucleotides comprising the substituent RH, as described above. They may also be selected from 2'-N—$C_3$-$C_7$-alkyl-amino-LNA nucleotides such as 2' (propyl, butyl, pentyl, hexyl, heptyl, cyclopentyl, methylcyclopentyl, ehtylcyclopentyl, cyclohexyl, methylcyclohexyl)-amino LNA where the definition of the alkyl moiety includes the constitutional isomers. They may also be selected from 2'-N—$C_3$-$C_7$-acyl-amino-LNA (or 2'N—C3-C7 amido LNA) nucleotides such as 2' (propyl, butyl, pentyl, hexyl, heptyl, cyclopentyl, methylcyclopentyl, ehtylcyclopentyl, cyclohexyl, methylcyclohexyl)-amido LNA wherein the definition of the alkyl moiety also includes the constitutional isomers. The nucleotides having a 2' hydrophobic substituent may also be selected from 2'-O-hydrocarbyl-RNA nucleotides such as 2'-O—$C_3$-$C_{26}$-alkyl-RNA monomer units or 2'-O—$C_6$-$C_{26}$-aryl-RNA nucleotide units or 2'-O-Alkyloxyhydrocarbyl-RNA monomer units such as 2'-O—$C_1$-$C_6$-alkyloxy-$C_3$-$C_{26}$-alkyl-RNA nucleotide units or 2'-O—$C_1$-$C_6$-alkyloxy-$C_6$-$C_{26}$-aryl-RNA monomer units, preferably from 2'O-Alkyl-RNA nucleotides having between 3 and 12 carbon atoms in their alkyl moiety, such as 2' O-propyl, butyl, pentyl, hexyl, heptyl, octyl, nonyl, decyl, undecyl, dodecyl, propylcyclopentyl, butylcyclopentyl, pentylcyclopentyl, methylcyclohexyl, ethylcyclohexyl, propylcyclohexyl, butylcyclohexyl, pentylcyclohexyl, hexylcyclohexyl RNA. Also with preference are selected 2' methoxyalkyl RNA nucleotide units having between 3 and 12 carbon atoms in their alkyl moiety. Other preferred 2'-O-hydrocarbyl RNA nucleotide are selected from a groups wherein the hydrocarbyl moiety has between 3 and 12 carbon atoms and comprises an aryl such as a phenyl, benzyl, toloyl, ethylphenyl, phenylethyl, propylphenyl, phenylpropyl or isopropylphenyl group or a butylphenyl or hexylphenyl group.

The number of hydrophobic nucleotide monomers in the oligo of this aspect of the invention is at least one. Generally, not more than 40%, preferably not more than 30%, more preferably not more than 20% of the total number of monomer units in the oligo are hydrophobic monomers. The number of hydrophobic nucleotides in the oligo may be from 1 to 8, preferably from 1 to 6, more preferably from 2 to 4.

The presence of at least one carboxylated (e.g. carboxyalkylated or carboxyarylated) 2' amino LNA nucleotide monomer units in the oligonucleotide of this invention is mandatory, the presence of a hydrophobic nucleotide units is optional and, in one embodiment, none is present. When hydrophobic nucleotides are present, the combined number of hydrophobic and carboxylated 2' amino LNA nucleotides is at least two. The combined portion of hydrophobic and carboxyalkylated or carboxyarylated 2' amino LNA nucleotides should not exceed 40% of all nucleotides of an oligo, preferably not more than 30%. In absolute terms, the combined number may be between 2 and 8, preferably between 2 and 6.

The single stranded oligonucleotides of this invention may have a sequence of nucleotides that is essentially identical or essentially complementary to a sequence found in the genome of an organism. Essentially identical or essentially complementary means that 10% or less of said sequence are not complementary or are missing in abasic sites, preferably that number is below 5%.

Said organism can be a eukaryotic organism such as a plant, a fungus or an animal. In preferred embodiments said organism is a mammal. In even more preferred embodiments said organism is a human.

Single stranded oligonucleotides having a sequence that is essentially identical or complementary to a genome act at the interior of a cell. In many cases such oligonucleotides interfere with the processing of RNA by various means such as inhibition of transcription, maturation or translation, proofreading, splicing and other intracellular processes.

It is known in the art that certain of these functions such as translation inhibition or mediation of alternative splicing, the competition with miRNA as described for anti-miR or antagomir compounds rely mainly on hydridization of the oligonucleotide with its intracellular target. Typically, these functions are less sensitive to a specific location of the hydrophobic nucleotide or the carboxylated nucleotide.

On the contrary, function that involve enzyme catalysis such as antisense oligonucleotides are sensitive to positional effects, a finding that lead to the development of the so-called gapmer architecture.

In an embodiment, the invention is directed to antisense oligonucleotides having between 10 to 30 nucleotides in a sequence that is essentially complementary to a sequence found in a transcribed mRNA or pre mRNA of a genome. In preferred antisense oligonucleotides the hydrophobic and/or carboxylated monomers of the oligo are located close to the 5' and/or 3' ends of the oligo, and may be absent in a central region of the oligo. In one embodiment, they are all present at nucleotide positions 1 to 5, preferably 1 to 3, from the 5'-end of the oligo, wherein the 5'-terminal monomer unit is position 1; and/or they are present at nucleotide positions t to (t-4), preferably t to (t-2), from the 3'-end of the oligo, whereby the 3'-terminal monomer unit is position t.

In one embodiment, the at least two carboxylated and/or hydrophobic monomers are all present in one of the half sequence segments of the oligo, i.e. either in the 5'-end half of the sequence or the 3'-end half of the sequence. In an alternative embodiment, at least one carboxylated and/or hydrophobic monomer is present in each of the half sequence segments of the oligo, i.e. at least one in the 5'-end half of the sequence and a least one in the 3'-end half of the sequence. In another embodiments where the oligo contains two carboxylated 2'-amino LNA units but no hydrophobic unit, the at least two, preferably two, carboxylated 2'-amino-LNA nucleotide units are all present in one of the half sequence segments of the oligo, i.e. either in the 5'-end half of the sequence or the 3'-end half of the sequence; or at least one, preferably one, carboxylated monomer is present in each of the half sequence segments of the oligo, i.e. at least one, preferably one, in the 5'-end half of the sequence and a least one, preferably one, in the 3'-end half of the sequence. The embodiments of this and the previous paragraph may be combined with the length definitions of the oligo given above, the preferred internucleoside linkages given above, the maximum numbers of nucleotide monomer units in the oligo given above, and/or with the numbers of the carboxylated −2'-amino-LNA in the oligo given above.

The inventor has surprisingly found that the oligonucleotides of the invention having one or more carboxylated (e.g. carboxyalkylated or carboxyarylated) 2' amino-LNA nucleotide units are useful e.g. as single stranded oligonucleotide therapeutics by displaying a greatly enhanced potency and specificity for their target. Thus, oligonucleotides of the invention are very useful e.g. for therapeutic purposes, as well as for diagnostic purposes, notably in vivo.

Oligonucleotides of this invention also have high transfection efficiency for eukaryotic cells even if no transfectants are used (unassisted delivery into cells). This does further support their usefulness, in particular for therapeutic applications.

The oligo of the invention may be used in therapy of an animal such as a mammal, and preferably in humans. The therapy may be therapy of cancer. The invention also provides the oligo of the invention for use as a medicament. The invention also provides the oligo of the invention for use in diagnostics such as molecular diagnostics. The invention also provides the oligo of the invention for use in disease prognostics. It will be apparent to the skilled person that the antisense and aptamer oligonucleotides of the invention can be designed to target specific genes and gene products.

The oligonucleotide of the invention may be used as a medicament. Once a therapeutic target has been validated, the skilled man can design the oligonucleotides that affect the level and the activity of the target, because the specificity of the antisense oligonucleotides lies exclusively within the sequence and composition of the antisense oligonucleotide. The invention also provides a pharmaceutical composition comprising the antisense oligonucleotide of the invention and a pharmaceutically acceptable excipient such as a diluent, a carrier or an adjuvant.

Pharmaceutical compositions comprising the oligonucleotide of the invention may be administered as known in the art in a physiologically acceptable medium (e.g., deionized water, phosphate buffered saline (PBS), saline, aqueous ethanol or other alcohol, plasma, proteinaceous solutions, mannitol, aqueous glucose, vegetable oil, or the like). Thus a further embodiment of the present invention relates to a pharmaceutical composition comprising the oligonucleotide with suitable excipients. Buffers may also be included, particularly where the media are generally buffered at a pH in the range of about 5 to 9, where the buffer will generally range in concentration from about 5 to 250 mM and wherein optionally salts are present, in a range from about 5 to 500 mM, physiologically acceptable stabilizers, and the like.

The oligonucleotide or the compositions may be lyophilized for convenient storage and transport. Thus, in a further embodiment of the present invention the composition comprises one or more excipients, diluents and/or carriers such as sucrose, trehalose, sorbitol and the like. Aqueous suspensions may contain the active materials in admixture with excipients suitable for the manufacture of aqueous suspensions. Such excipients include suspending agents, for example sodium carboxymethylcellulose, methylcellulose, hydroxypropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. Another possible excipient is albumin such as human serum albumin.

The aqueous suspensions can also contain one or more preservatives, for example ethyl or n-propyl p-hydroxybenzoate, one or more coloring agents, one or more flavoring agents, and one or more sweetening agents, such as sucrose or saccharin. However, it is preferred that the pharmaceutical composition does not include preservatives, but is sterile and packed in single-dose units.

The aqueous suspension of the oligonucleotide or the lyophilized form the same may also be packaged into gelatin capsules or other systems effectively reaching the gastrointestinal tract.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient (e.g. in lyophilised form) in admixture with a dispersing or wetting agent, suspending agent and one or more preservatives.

Suitable dispersing or wetting agents or suspending agents are exemplified by those already mentioned above. Additional excipients, for example sweetening, flavoring and coloring agents, can also be present. Compositions of the invention can also be in the form of oil-in-water emulsions. The oily phase can be a vegetable oil or a mineral oil or mixtures of these.

Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example, sorbitan monooleate, and condensation products of the said partial esters with ethylene oxide, for example polyoxyethylene sorbitan monooleate. The emulsions can also contain sweetening and flavoring agents. Compounds of the invention can be administered parenterally in a sterile medium.

The oligonucleotide alone or in combination with excipients, depending on the vehicle and concentration used, can either be suspended or dissolved in the vehicle. Advantageously, adjuvants such as local anesthetics, preservatives and buffering agents can be dissolved in the vehicle.

As also known in the art, the oligonucleotide and the pharmaceutical compositions are generally administered parenterally, such as intravascularly (IV), intraarterial (I.A), intramuscularly (I.M), subcutaneously (SC), mucosally, orally or the like. Administration may also be made by transfusion, or it may be mucosal, oral, nasal, rectal, transdermal or aerosol, where the nature of the conjugate allows for transfer to the vascular system. Usually a single injection will be employed, although more than one injection may be used, if desired. Administration may by any convenient means, including syringe, trocar, catheter, or the like. The particular manner of administration will vary depending upon the concentration to be administered, whether a single bolus or continuous administration, or the like. The administration can be intravascularly, where the site of introduction is not critical to this invention, preferably at a site where there is rapid blood flow, (e.g., intravenously, peripheral or central vein). Preferably, the route of administration is mucosal or oral. Other administration routes may be useful, e.g. where the administration is coupled with slow release techniques or a protective matrix such as gelatin capsules.

Dosage levels of the oligonucleotide as active ingredient are on the order of from about 0.01 mg to about 10 mg per kilogram of body weight per day are useful in the treatment of the described conditions (about 0.5 mg to about 1 g per patient per day). The amount of active ingredient that can be combined with the carrier materials to produce a single dosage form may vary depending upon the host treated and the particular mode of administration. The concentration of the oligonucleotide for administration may range from about 1 pg/ml to 100 mg/ml, pre-administration. The total amount administered intravascularly will generally be in the range of about 0.1 mg to about 500 mg, preferably about 1 mg to about 250 mg.

The composition of the present invention may be formulated for the intended use. Thus, one embodiment of the present invention relates to a composition that is formulated for oral or mucosal administration.

Medical Use and Treatment

The oligonucleotide or the pharmaceutical compositions may be used to treat diseases in a mammal in which inhibition of gene expression of a particular gene is beneficial. "Mammal" for purposes of treatment refers to any animal classified as a mammal, including humans, domestic and farm animals, and zoo, or sports, animals, such as dogs, horses, cats, cows, etc. Preferably, the mammal is human. The diseases that may be treated are diseases that can be treated by down-regulating or silencing a gene or its product, such as those given in WO 2014/005596. Such diseases include, but are not limited to, cancer, autoimmune diseases, viral and bacterial infections, endocrine system disorders, neural disorders including central and peripheral nervous system disorders, cardiovascular disorders, pulmonary disorders, and reproductive system disorders.

In one embodiment of the invention, the oligonucleotide and compositions of the invention are useful for the amelioration and/or treatment of cancers and other hyperproliferative disorders. Cancer cells are usually characterized by aberrant expression of a gene. Cancers and other hyperproliferative disorders for which this invention provides therapy include, but are not limited to, neoplasms associated with connective and musculoskeletal system tissues, such as fibrosarcoma, rhabdomyosarcoma, myxosarcoma, chondro sarcoma, osteogenic sarcoma, chordoma, and liposarcoma, neoplasms located in the abdomen, bone, brain, breast, colon, digestive system, endocrine glands (adrenal, parathyroid, pituitary, testicles, ovary, thymus, thyroid), eye, head and neck, liver, lymphatic system, nervous system (central and peripheral), pancreas, pelvis, peritoneum, skin, soft tissue, spleen, thorax, and urogenital tract, leukemias (including acute promyelocytic, acute lymphocytic leukemia, acute myelocytic leukemia, myeloblasts, promyelocytic, myelomonocytic, monocytic, erythroleukemia), lymphomas (including Hodgkins and non-Hodgkins lymphomas), multiple myeloma, colon carcinoma, prostate cancer, lung cancer, small cell lung carcinoma, bronchogenic carcinoma, testicular cancer, cervical cancer, ovarian cancer, breast cancer, angiosarcoma, lymphangiosarcoma, endotheliosarcoma, lymphangioendotheliosarcoma, synovioma, mesothelioma, Ewing's sarcoma, leiomyosarcoma, squamous cell carcinoma, basal cell carcinoma, pancreatic cancer, renal cell carcinoma, Wilm's tumor, hepatoma, bile duct carcinoma, adenocarcinoma, epithelial carcinoma, melanoma, sweat gland carcinoma, sebaceous gland carcinoma, papillary carcinoma, papillary adenocarcinoma, glioma, astrocytoma, medulloblastoma, craniopharyngioma, ependymoma, pinealoma, emangioblastoma, acoustic neuroma, oligodendroglioma, menangioma, neuroblastoma, retinoblastoma, bladder carcinoma, embryonal carcinoma, cystadenocarcinoma, medullary carcinoma, choriocarcinoma, and seminoma.

Thus, an aspect of the present invention relates to the use of oligonucleotide as described herein for treatment of diseases that benefit from intestinal delivery e.g. cancer, inflammatory disease as described above.

Another aspect of the present invention relates to the use of oligonucleotide as described herein for intestinal delivery of a drug. Yet another application of the present invention relates to regulating genetic expression of a transcript or protein associated with a disease. A further application of the present invention relates to a method of treating a disease, comprising administration of the oligonucleotide or the composition of the present invention to a mammal in need thereof.

The invention further provides a method of mediating nucleic acid modification of a target nucleic acid in a cell or an organism comprising the steps:
  a. contacting a cell or organism with an antisense oligonucleotide of the invention under conditions wherein modification of a target nucleic acid can occur; and
  b. thereby mediating modification of a target nucleic acid.

The method of mediating nucleic acid modification of a target nucleic acid may be performed in vitro or in vivo, i.e. in animals such as mammals, or in humans. The method of mediating nucleic acid modification of a target nucleic acid may, alternatively, be performed in cell cultures or on an isolated cell. In a preferred embodiment, the nucleic acid modification of the method is gene silencing (=down regulation of gene expression), preferably degradation of target mRNA or translational inhibition of target mRNA or inhibition of other types of RNA, e.g. non-coding RNA. Accordingly, the invention provides a method of mediating gene silencing in a cell or an organism, comprising contacting said cell or organism with an antisense oligonucleotide of the invention. In another embodiment, the invention provides a method of modulating splicing events in a cell or an organism like a human to provide gene products that are able to alleviate diseases which have malfunctioning RNA-splicing as a cause.

Another aspect of the invention is a method of examining the function of a gene in a cell or organism, comprising:
a. introducing an antisense oligonucleotide of the invention corresponding to said gene into the cell or organism, thereby producing a test cell or test organism
b. maintaining the test cell or test organism under conditions under which modification of a target nucleic acid can occur; and
c. observing the phenotype of the test cell or organism produced in step b and optionally comparing the observed phenotype with the phenotype of an appropriate control cell or control organism, thereby providing information about the function of the gene.

The cell is preferably a cell of an animal such as a mammalian or human cell. In preferred embodiments of the method of examining the function of a gene in a cell or organism, the method is performed in cell cultures, in vitro or in vivo. In yet another embodiment, the method is performed on an isolated cell.

The antisense oligonucleotides of the invention can be introduced into cells e.g. using transfection or gymnotic delivery, as known to a person skilled in the art. The oligonucleotides may be introduced into an organism e.g. by intravenous or subcutaneous injection, which is known to the skilled person, or by other methods of introduction known to the skilled person.

The information obtained about the function of a gene may be used to determine whether a gene product is a suitable target for therapeutic intervention in relation to a particular disease. Thus, if it is demonstrated that a certain gene product acts in a certain biochemical pathway known to be affected in e.g. a specific subtype of cancer, the gene product might be a suitable target for therapeutic intervention for treatment of the aforementioned subtype of cancer.

In a preferred embodiment of the method of examining the function of a gene in a cell or organism, the nucleic acid modifications of the method is gene silencing (=down regulation of gene expression), preferably degradation of target mRNA or translational inhibition of target RNA.

Another aspect of the invention is a method of assessing whether an agent acts on a gene product comprising the steps:
a. introducing an antisense oligonucleotide of the invention corresponding to said gene into a cell or organism, thereby producing a test cell or test organism;
b. maintaining the test cell or test organism under conditions under which modification of a target nucleic acid occurs;
c. introducing the agent into the test cell or test organism; and
d. observing the phenotype of the test cell or test organism produced in step c and optionally comparing the observed phenotype with the phenotype of an appropriate control cell or control organism, thereby providing information about whether the agent acts on the gene product.

In a preferred embodiment of the method of assessing whether an agent acts on a gene or gene product, the nucleic acid modification of the method is gene silencing (=down regulation of gene expression), preferably degradation of target RNA or translational inhibition of target RNA. In preferred embodiments of the method of assessing whether an agent acts on a gene product, the method is performed in cell cultures, in vitro or in vivo. In yet another embodiment, the method is performed on an isolated cell.

Oligonucleotides of the invention are also useful for research purposes. It is for example well-known how oligonucleotides, including chemically modified oligonucleotides, can be used to study the function of a gene. This involves the addition of the oligonucleotide to a cell culture under conditions where cell membrane penetration is possible. By designing the sequence to be complementary to the target gene, or the target nucleic acid, the effect of such RNA/nucleic acid targeting can be evaluated. This enables for example the evaluation of the importance and effect of expression of that given gene. This research therefore can be important to evaluate the relevance of expression of a given gene, e.g. the protein encoded by such gene, for the development of a given disease. Thus, the invention also provides a reagent containing an oligonucleotide according to the invention. The reagent may further contain an excipient such as any one or more of those mentioned above.

DESCRIPTION OF THE FIGURES

FIG. 2A demonstrates the inhibition of cell growth using oligonucleotides targeting the Eg5 gene, whereas FIG. 2B shows the data obtained using control, non-targeting oligonucleotides comprising the exact same modifications.

EXAMPLES

Figure 1A:
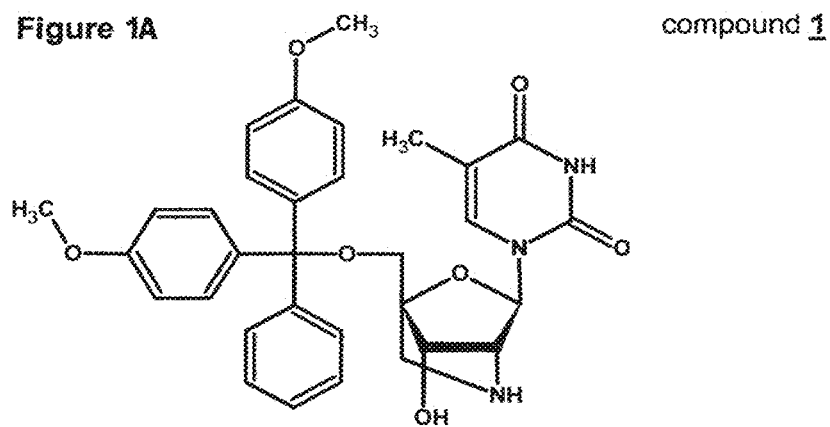
FIGS. 1A-1F: Compounds obtained during the synthesis of the examples and used for the preparation of the modified oligonucleotides
Figure 1B:
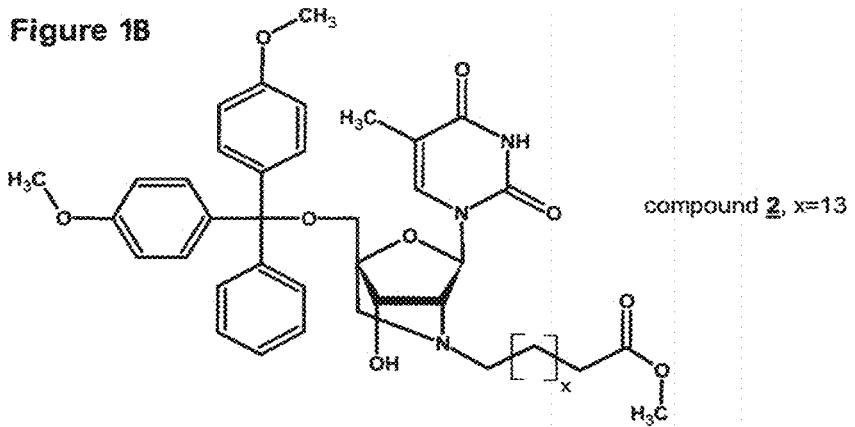
Figure 1C:
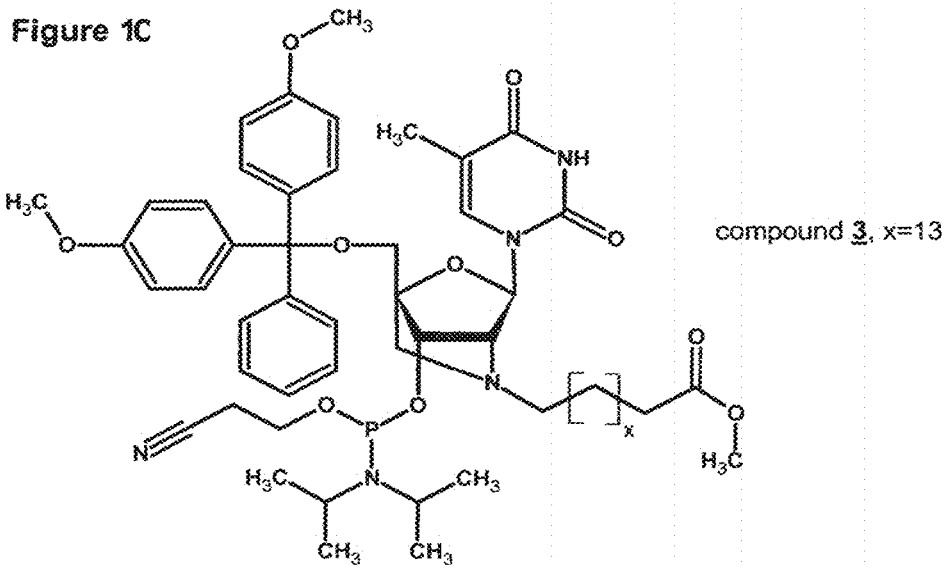
Figure 1D:
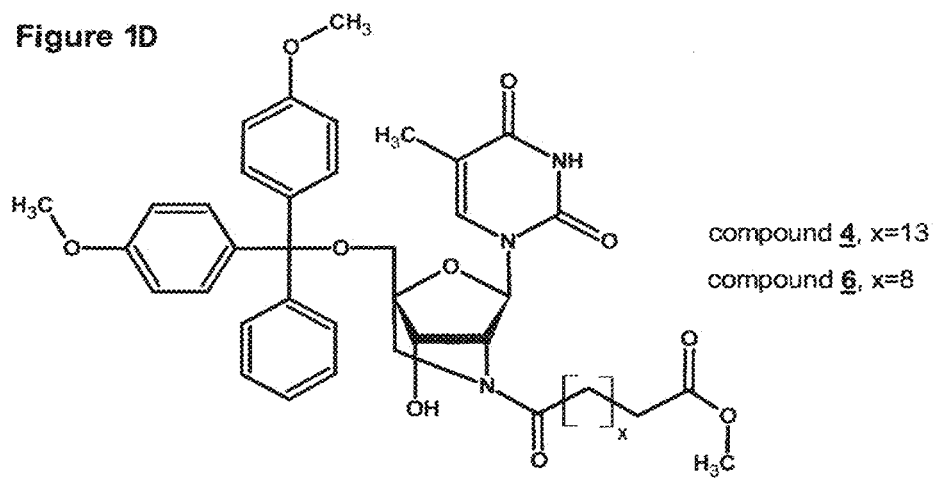
Figure 1E:
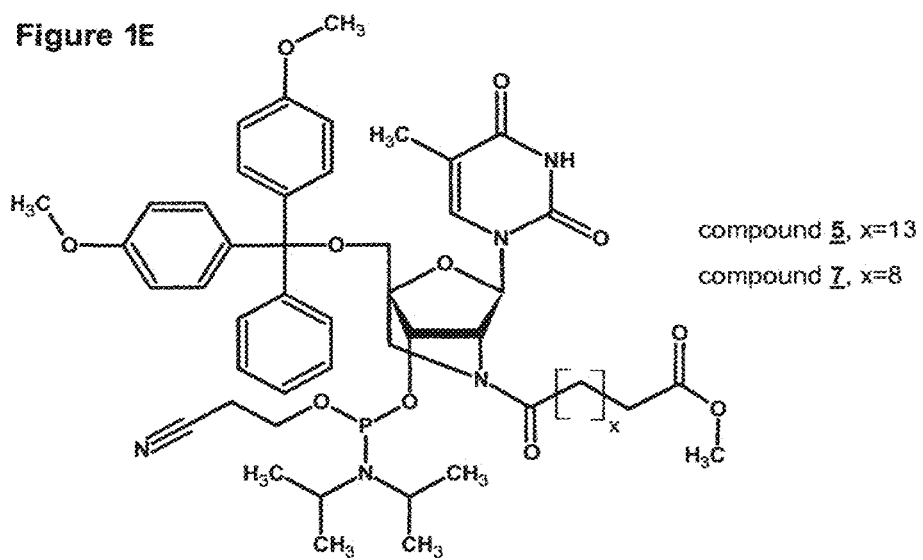
Figure 1F:
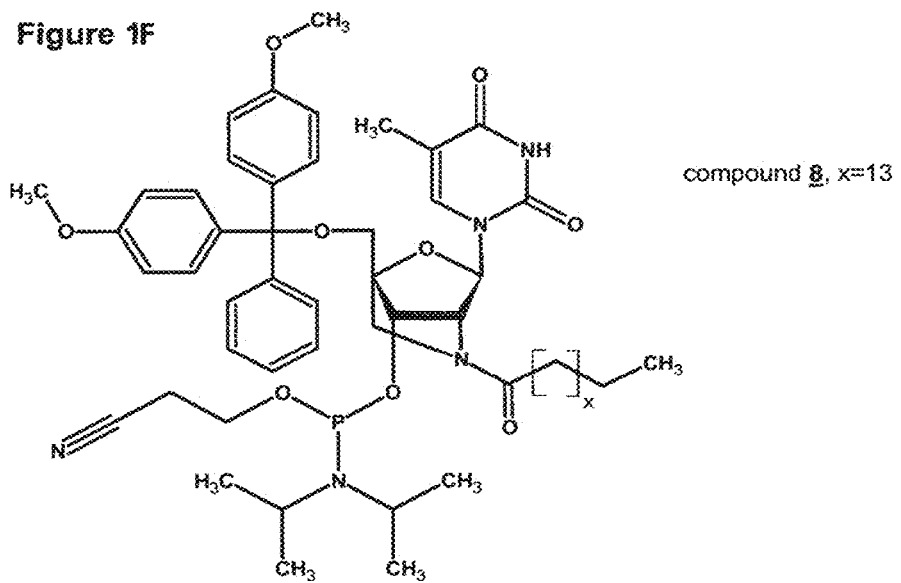

The following examples illustrate, but not limit the invention:

Example 1—Preparation of a Carboxyalkylated 2' Amino LNA 1 g of the 5' DMTO protected 2'amino LNA thymidine 1 was brought in 40 mL dichloromethane and 0.4 mL acetic acid were added; the mixture was placed on ice. 498 mg of 16 oxo-hexadecanoic acid methyl ester were dissolved in 20 mL dichloromethane and given to the amino LNA. 275 mg sodium cyanoborohydride in 10 mL methanol were added dropwise to the solution. The ice was removed and the components were allowed to react overnight at room temperature. The carboxyalkylated 2' amino LNA was isolated using ethyl acetate:brine and chromatographed on silica using petrol ether:ethyl acetate as solvent. 1.2 g of 2 were obtained.

Example 2-Phosphoamidate of the Carboxyalkylated 2' Amino LNA 0.95 g of 2 were dissolved in 20 ml absolute dichloromethane and placed on ice. 585 mg of dry N,N-Diisopropylethylamine were added followed by 2 portions of 401 mg of 2-Cyanoethyl N,N-diisopropylchlorophosphoramidite (3-([Chloro(diisopropylamino)phosphanyl]oxy)-propanenitrile) in 5 mL dichloromethane each. Total reaction time was 24 h at room temperature. The organic phase was extracted two time with saturated sodium hydrogen carbonate and purified over silica using ethyl acetate as solvent. 800 mg of the phosphoamidate 3 were isolated.

Example 3—Oligonucleotides Comprising Carboxyalkylated 2' Amino LNA

Gapmer antisense oligonucleotides were synthesized with the following sequences and modification patterns (noted in 5'-3' direction):

TABLE 3

List of certain oligonucleotides targeting the Eg5 gene.

| Seq ID | Nucleotide | T | C | C | A | A | G | T | G | C | T | A | C | T | G | T | A |
|---|---|---|---|---|---|---|---|---|---|---|---|---|---|---|---|---|---|
|  | DNA |  |  |  | d | d | d | d | d | d | d | d | d |  |  |  | d |
|  | LNA | b | b | b |  |  |  |  |  |  |  |  |  | b | b | b |  |
|  | special |  |  |  |  |  |  |  |  |  |  |  |  |  |  |  |  |
|  | special | c16 |  |  |  |  |  |  |  |  |  |  |  |  |  | c16 |  |
|  | special | a16 |  |  |  |  |  |  |  |  |  |  |  |  |  | a16 |  |
|  | special | a16 |  |  |  |  |  |  |  |  |  |  |  |  |  | a16 |  |
|  | Backbone |  |  |  |  |  |  |  |  |  |  |  |  |  |  |  |  |
| 1 | s | Tbs | Cbs | Cbs | dAs | dAs | dGs | dTs | dGs | dCs | dTs | dAs | dCs | Tbs | Gbs | Tbs | dA |
| 2 | s | Tbc16s | Cbs | Cbs | dAs | dAs | dGs | dTs | dGs | dCs | dTs | dAs | dCs | Tbs | Gbs | Tbc16s | dA |
| 3 | s | Tba16s | Cbs | Cbs | dAs | dAs | dGs | dTs | dGs | dCs | dTs | dAs | dCs | Tbs | Gbs | Tba16s | dA |
| 4 |  | Tb | Cb | Cb | dA | dA | dG | dT | dG | dC | dT | dA | dC | Tb | Gb | Tb | dA |
| 5 |  | Tbc16 | Cb | Cb | dA | dA | dG | dT | dG | dC | dT | dA | dC | Tb | Gb | Tbc16 | dA |
| 6 |  | Tba16 | Cb | Cb | dA | dA | dG | dT | dG | dC | dT | dA | dC | Tb | Gb | Tba16 | dA |

TABLE 4

List of certain control oligonucleotides not targeting any human or mouse gene.

| Seq ID | Nucleotide | T | C | C | A | A | G | T | G | C | T | A | C | T | G | T | A | G | T | A |
|---|---|---|---|---|---|---|---|---|---|---|---|---|---|---|---|---|---|---|---|---|
|  | DNA |  |  |  | d | d | d | d | d | d | d | d | d | d | d |  |  |  |  |  |
|  | LNA | b | b | b | b |  |  |  |  |  |  |  |  |  |  | b | b | b | b |  |
|  | special |  |  |  |  |  |  |  |  |  |  |  |  |  |  |  |  |  |  |  |
|  | special | c16 |  |  |  |  |  |  |  |  |  |  |  |  |  |  |  |  | c16 |  |
|  | special | a16 |  |  |  |  |  |  |  |  |  |  |  |  |  |  |  |  | a16 |  |
|  | special | a16 |  |  |  |  |  |  |  |  |  |  |  |  |  |  |  |  | a16 |  |
|  | Backbone |  |  |  |  |  |  |  |  |  |  |  |  |  |  |  |  |  |  |  |
| 7 | s | Tbs | Cbs | Cbs | Abs | dAs | dGs | dTs | dGs | dCs | dTs | dAs | dCs | dTs | dGs | Tbs | Abs | Gbs | Tbs | dA |
| 8 | s | Tbc16s | Cbs | Cbs | Abs | dAs | dGs | dTs | dGs | dCs | dTs | dAs | dCs | dTs | dGs | Tbs | Abs | Gbs | Tbc16s | dA |
| 9 | s | Tba16s | Cbs | Cbs | Abs | dAs | dGs | dTs | dGs | dCs | dTs | dAs | dCs | dTs | dGs | Tbs | Abs | Gbs | Tba16s | dA |
| 10 |  | Tb | Cb | Cb | Ab | dA | dG | dT | dG | dC | dT | dA | dC | dT | dG | Tb | Ab | Gb | Tb | dA |
| 11 |  | Tbc16 | Cb | Cb | Ab | dA | dG | dT | dG | dC | dT | dA | dC | dT | dG | Tb | Ab | Gb | Tbc16 | dA |
| 12 |  | Tba16 | Cb | Cb | Ab | dA | dG | dT | dG | dC | dT | dA | dC | dT | dG | Tb | Ab | Gb | Tba16 | dA |

Symbols

A,C,G,T denote nucleobases d before nucleobase=DNA nucleobase followed by b=LNA (a conventional 2,4-methoxyribose-LNA)

c16 denotes the carboxylated 2' amino LNA from example 1 a16 denotes a palmitoylated 2' amino LNA s stands for phosphorothioate internucleoside linkage where "s" is absent, the internucleoside linkage is a phosphodiester.

The oligonucleotides having the sequence ID1 to 12 were synthesized on an Expedite 8909 synthesized using the RNA coupling protocol of the supplier at a 1 µmol scale. At the end of the synthesis cycle, oligonucleotides were cleaved from their support using 0.5M sodium hydroxide in methanol/water (5:1) for 30 min at room temperature. The material was further incubated for 10 hours at room temperature to afford deprotection and cleavage of the methyl ester from the carboxylated 2' amino LNA. The solution was desalted using NAP10 columns and lyophilized and the material was purified using anion exchange.

Example 4—Preparation of Carboxyalkylated 2' Amido LNA

Hexadecanedioic acid monomethyl ester was prepared and activated as NHS ester. 25 g hexadecanedioic acid dimethyl ester were dissolved in 250 mL methanol and 25 g barium hydroxide octahydrate in 200 mL methanol were added dropwise. Upon completion 500 mL ice water, 200 mL 1N HCl were added and extracted using ethylacetate. The organic phase was reduced to a small volume and hexadecanedioic acid monomethyl ester was crystallized in the cold, filtered and dried. 1 g of the material was dissolved in 25 mL THF and 0.46 g N-Hydroxysuccinimide and 0.89 g N,N'-Dicyclohexylcarbodiimide were added. The reaction mixture was stirred overnight, reduced under vacuum, heated under reflux upon addition of 50 mL hexane and 5 mL ethylacetate and filtered while hot. The filtrate was reduced under vaccum and the NHS ester of hexadecanedioic acid monomethyl ester precipitated in the cold.

The conjugate 4 of hexadecanedioic acid monomethyl ester with the 2' amido LNA thymidine 1 was prepared from equimolar components. 0.45 g 1 and 0.313 g of the NHS ester of hexadecanedioic acid monomethyl ester were dissolved in 10 mL THF. 0.11 mL trimethylamine was added and the mixture was stirred at 40° C. for 2 days. The conjugate 4 was purified from the reaction mixture on silica using ethylacetate and methanol as solvents. Early eluting material was re-purified on silica to 90% purity.

The C11 homologue 6 was prepared on the same route.

Example 5—Phosphoramidates of the Carboxyalkylated 2' Amido LNA 0.35 g of 4 or 6 were dissolved in 10 ml absolute dichloromethane and placed on ice. 212 mg of dry N,N-diisopropylethylamine were added followed by 145 mg of 2-cyanoethyl N,N-diisopropylchlorophosphoramidite (3-([Chloro(diisopropylamino)phosphanyl]oxy)-propanenitrile) in 5 mL dichloromethane. Total reaction time was 24 h at room temperature. The organic phase was extracted two time with saturated sodium hydrogen carbonate and purified over silica using ethyl acetate as solvent. 300 mg of the phosphoramidate 5 were isolated using 4 as a precursor. 315 mg of the phosphoramidate 7 were isolated using 6 as a precursor.

Example 6—A series of Oligonucleotides Comprising Carboxyalkylated 2' Amino LNA or 2' Amido LNA Gapmer antisense oligonucleotides targeting the Eg5 gene or respective mismatch controls were synthesized. The parent sequence was taken from Koller et al. (2006) in Cancer Res 66 (4): 2059-2066.

The C16 carboxyalkylated LNA amine 3 or the C16 carboxyalkylated LNA Amide 5 were inserted into the sequence as indicated in the table below. In addition, a C16 alkylated LNA Amide 8 was used, synthesis described in I. K. Astakhova and J. Wengel, *Acc. Chem. Res.*, 2014, 47, 1768. The sequences and modification patterns (noted in 5'-3' direction) are as follows:

TABLE 5

List of certain oligonucleotides targeting the Eg5 gene.

| Eg5 on-target | | | T | C | C | A | A | G | T | G | C | T | A | C | T | G | T | A | G | T | A |
|---|---|---|---|---|---|---|---|---|---|---|---|---|---|---|---|---|---|---|---|---|---|
| | | DNA | | | | | | d | d | d | d | d | d | d | d | d | | | | | d |
| | | LNA | b | b | b | b | | | | | | | | | | | b | b | b | b | |
| Group | SeqID | Modification | | | | | | | | | | | | | | | | | | | |
| Parent | 16/38 | | | | | | | | | | | | | | | | | | | | |
| Amide C | 47 | C | 5 | | | | | | | | | | | | | | | | | | |
| | 17/35 | CC | 5 | | | | | | | | | | | | | | | | 5 | | |
| | 17/37 | CCC | 5 | | | | | | | | | | | | | | 5 | | 5 | | |
| Amine C | 51 | C-C | 3 | | | | | | | | | | | | | | | | 3 | | |
| | 53 | C-CC | 3 | | | | | | | | | | | | | | 3 | | 3 | | |
| Amine C/ | 59 | A-C | 8 | | | | | | | | | | | | | | | | 3 | | |
| Amide A | 55 | A-CC | 8 | | | | | | | | | | | | | | 3 | | 3 | | |
| mixed | 61 | A-AC | 8 | | | | | | | | | | | | | | 8 | | 3 | | |
| | 63 | C-AC | 3 | | | | | | | | | | | | | | 8 | | 3 | | |

Symbols A,C,G,T in the first line denote the nucleobases, numbers 3, 5 or 8 denote the modified 2'amino or 2' amido LNA compounds used for the synthesis of the oligonucleotide. Within the modification patterns "C" denotes a carboxyalkylated 2' amino LNA or a carboxyalkylated 2' amido LNA and "A" denotes an alkylated 2' amino LNA.

For comparison, a mutated, non-targeting sequences was used. The C16 carboxyalkylated LNA amine 3 or the C16 carboxyalkylated LNA Amide 5 were inserted into the non-targeting sequence as indicated in the table below. In addition, a C16 alkylated LNA Amide 8 was used, synthesis described in I. K. Astakhova and J. Wengel, *Acc. Chem. Res.*, 2014, 47, 1768. The sequences and modification patterns (noted in 5'-3' direction) are as follows:

TABLE 6

List of certain control oligonucleotides not targeting any human or mouse gene.

| Mismatch Controls | | | T | A | C | G | C | C | T | T | C | T | A | T | T | C | T | C | A | T | G |
|---|---|---|---|---|---|---|---|---|---|---|---|---|---|---|---|---|---|---|---|---|---|
| | Seq ID | DNA | | | | | d | d | d | d | d | d | d | d | d | | | | | | d |
| | | LNA | b | b | b | b | | | | | | | | | | b | b | b | b | | |
| Group | Seq ID | Modification | | | | | | | | | | | | | | | | | | | |
| Control | 16/39 | | | | | | | | | | | | | | | | | | | | |
| Amide C | 46 | C | 5 | | | | | | | | | | | | | | | | | | |
| | 17/36 | CC | 5 | | | | | | | | | | | | | | | | 5 | | |
| | 17/38 | CCC | 5 | | | | | | | | | | | | | | 5 | | 5 | | |
| Amine C | 52 | C-C | 3 | | | | | | | | | | | | | | | | 3 | | |
| | 54 | C-CC | 3 | | | | | | | | | | | | | | 3 | | 3 | | |
| Amine C/ | 60 | A-C | 8 | | | | | | | | | | | | | | | | 3 | | |
| Amide A | 56 | A-CC | 8 | | | | | | | | | | | | | | 3 | | 3 | | |
| mixed | 62 | A-AC | 8 | | | | | | | | | | | | | | 8 | | 3 | | |
| | 64 | C-AC | 3 | | | | | | | | | | | | | | 8 | | 3 | | |

Symbols A,C,G,T in the first line denote the nucleobases, numbers 3, 5 or 8 denote the modified 2'amino or 2' amido LNA compounds used for the synthesis of the oligonucleotide. Within the modification patterns "C" denotes a carboxyalkylated 2' amino LNA or a carboxyalkylated 2' amido LNA and "A" denotes an alkylated 2' amino LNA.

Example 7—Transfection of Cells

HeLa cells were grown in RPMI plus 10% FCS using 96 well microplates. Cells were seeded at a density of 3000 cells per well in 100 μl medium, grown over night and transfected with the oligonucleotides as follows: oligonucleotides were dissolved at 100 μM in 20 mM NaCl. Serial dilutions of this concentrated stock were prepared using Opti-MEM as diluent and transfection complexes were formed using lipofectamine 3000. 10 μl of said complexes were added to the cells to arrive at final concentration between 10 pM and 250 nM. The cells were incubated at 37° C., 5% CO2 and 100% humidity for 72 hours and cell viability was determined at the end of this period using a Cell Titer Blue cell viability assay (Promega, USA). A low cell viability can result from a specific inhibition of the Eg5 gene and resulting cell cycle arrest, it can also be caused by unspecific toxicity of the compounds or of the transfectant. To differentiate between the two, parallel experiments were performed using the Eg5 on-target compounds and their respective mismatch controls.

Figure 2A:
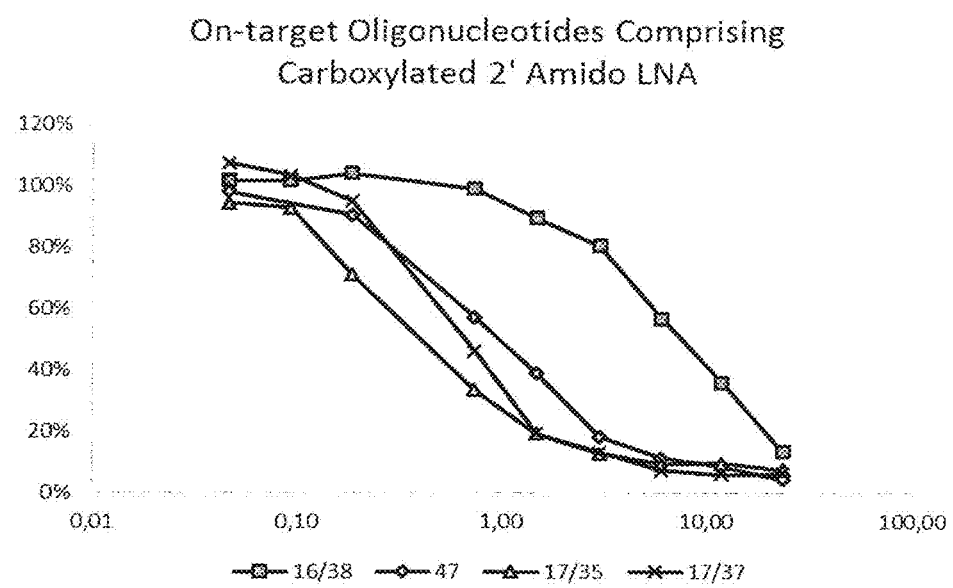
FIGS. 2A-2B: The dose response curves for oligonucleotides comprising one, two or three of the carboxylated 2' amido LNA modifications.
Figure 2B:
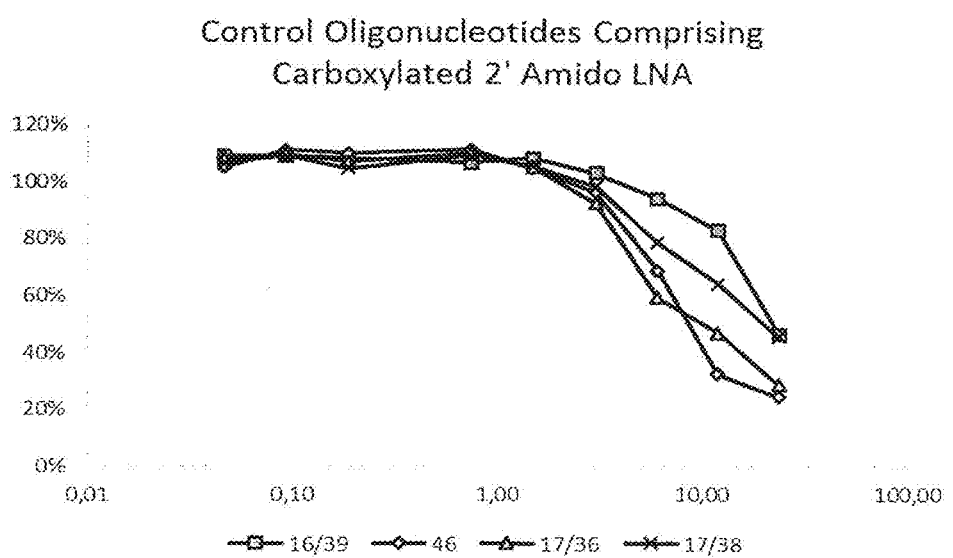

Example 8—Efficacy and Specificity of Oligonucleotides Comprising a Carboxylated 2' Amido LNA Oligonucleotides comprising carboxylated 2' amido LNA have a much improved efficacy and specificity. See FIGS. 2A and 2B. When compared to the parent compound 16/38, the oligonucleotide carrying a single C16 carboxylated 2' amido LNA (SeqID 47) was about 10 fold more potent. Introduction of a second and third modification in Seq ID 17/35 and 17/37 gave oligonucleotides having 20 to 70 fold better potency. The modified oligonucleotides also feature an improved specificity, as demonstrated in table 7.

TABLE 7

Potency and specificity of oligonucleotides comprising carboxyalkylated 2' amido LNA.

| Group | Modification | SeqID | EC50 in nM | Seq ID | EC50 in nM | specificity |
|---|---|---|---|---|---|---|
| Parent | | 16/38 | 7.6 | 16/39 | 23 | 3 |
| Amide C | C | 47 | 0.85 | 46 | 11 | 13 |
| | CC | 17/35 | 0.1 | 17/36 | 11 | 115 |
| | CCC | 17/37 | 0.3 | 17/38 | 18 | 60 |

Example 9—Efficacy and Specificity of Oligonucleotides Comprising a Carboxylated 2' Amino LNA Oligonucleotides comprising carboxylated 2' amino LNA feature improved efficacy and specificity. When compared to the parent compound 16/38, the oligonucleotide carrying a double C16 carboxylated 2' amino LNA (SeqID 51) was about 10 fold more potent. Introduction of a third modification in Seq ID 53 gave oligonucleotides having a potency similar to the parent compound, but much improved specificity.

TABLE 8

Potency and specificity of oligonucleotides comprising carboxyalkylated 2' amino LNA.

| Group | Modification | SeqID | EC50 in nM | Seq ID | EC50 in nM | specificity |
|---|---|---|---|---|---|---|
| Parent | | 16/38 | 1.5 | 16/39 | 23 | 5 |
| Amine C | CC | 51 | 0.2 | 52 | 25 | 151 |
| | CCC | 53 | 7.5 | 54 | 470 | 62 |

Example 10—Efficacy and Specificity of Oligonucleotides Comprising a Carboxylated 2' amino LNA in Combination with Alkylated 2' Amido LNA This example compares the potency and specificity of oligonucleotides comprising carboxylated 2' amino LNA in combination with alkylated 2' amido LNA, specifically the palmitoylated 2' amido LNA described in I. K. Astakhova and J. Wengel, Acc. Chem. Res., 2014, 47, 1768.

For oligonucleotides comprising two modified position such as SeqID 51 or 59, a replacement of a carboxylated with an alkylated 2' LNA resulted in somewhat reduced potency, but a stronger loss of specificity.

For oligonucleotides comprising three modified position such as SeqID 53 or the group of 55, 63, 61 a replacement of a single carboxylated with an alkylated 2' LNA resulted in a slightly reduced potency and specificity. A second replacement rendered the compound inactive.

TABLE 9

Potency and specificity of oligonucleotides comprising carboxyalkylated 2' amino LNA and mixed modifications of carboxyalkylated 2' amino LNA and alkylated 2' amido LNA.

| Modification | SeqID | EC50 in nM | Seq ID | EC50 in nM | specificity |
|---|---|---|---|---|---|
| CC | 51 | 0.3 | 52 | 10.6 | 35 |
| A-C | 59 | 1.1 | 60 | 3.8 | 4 |
| CCC | 53 | 1.3 | 54 | 89 | 70 |
| A-CC | 55 | 1.7 | 56 | 20.2 | 12 |
| C-AC | 63 | 2.7 | 64 | 28 | 10 |
| A-AC | 61 | >250 | 62 | >250 | |

The invention claimed is:

1. An oligonucleotide comprising from 3 to 100 nucleotide units, wherein at least one nucleotide unit independently copmrises a carboxylated 2'-amino locked nucleic acid (LNA) nucleotides of formula (1')

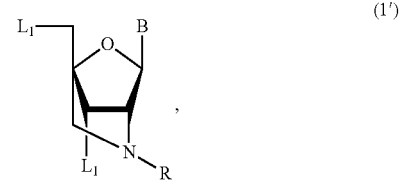

wherein:
B is a nucleobase,
each of $L_1$ is independently an internucleoside linkage, a bond to a neighboring nucleotide unit or a terminal moiety selected from the group consisting of —OH, phosphate, and a linker for the conjugation of the oligonucleotide to another molecule, and R is a carboxylated substituent comprising one or two carboxyl group(s) and wherein R comprises from 6 to 40 carbon atoms and from 0 to 3 heteroatoms selected from the group consisting of O, N, and S.

2. The oligonucleotide according to claim 1, wherein said oligonucleotide comprises from 5 to 50 nucleotides and is double stranded.

3. The oligonucleotide according to claim 1, wherein R has from 6 to 20 carbon atoms.

4. The oligonucleotide according to claim 1, wherein said carboxylated substituent is a carboxyhydrocarbyl group or a carboxyheterohydrocarbyl group, the carboxyheterohydrocarbyl group comprises from 1 to 3 heteroatoms selected from the group consisting of O, N, and S.

5. The oligonucleotide according to claim 1, wherein said carboxylated substituent is a carboxyalkyl substituent or a carboxyaryl substituent.

6. The oligonucleotide according to claim 1, wherein the internucleoside linkage is selected from phosphodiester, phosphorothioate, or phosphotriester linkage.

7. The oligonucleotide according to claim 1, wherein less than 40% of the total number of nucleotide units in the oligonucleotide are carboxylated 2'-amino LNA nucleotide units of the general formulas (1').

8. The oligonucleotide according to claim 1, wherein said oligonucleotide contains at most 8 of said carboxylated 2'-amino LNA nucleotide units of formula (1').

9. The oligonucleotide according to claim 1, wherein said oligonucleotide has, from the 5'-end to the 3'-end, three segments: a 5'-end segment of at least 2 nucleotide units, a central binding segment of at least 6 nucleotide units in length, and a 3'-end segment of at least 2 nucleotide units in length, and wherein said oligonucleotide contains at least one carboxylated 2'-amino-LNA nucleotide in each of said end segments, but none in the central segment.

10. The oligonucleotide according to claim 1, wherein at least one nucleotide unit is a hydrophobic nucleotide unit independently selected from the group consisting of:

2' amino LNA nucleotide moieties carrying on said 2'-amino group a (hetero)hydrocarbyl substituent comprising from 8 to 40 carbon atoms and from 0 to 3 heteroatoms selected from the group consisting of O, N, and S;

2'-N—$C_3$-$C_7$-alkyl-amino-LNA nucleotide moieties;

2'-N—$C_3$-$C_7$-alkyl-amido-LNA nucleotide moieties;

2'-O—$C_3$-$C_{26}$-alkyl-RNA nucleotide moieties;

2'-O—$C_6$-$C_{26}$-aryl-RNA nucleotide moieties,

2'-O—$C_1$-$C_6$-alkyloxy-$C_3$-$C_{26}$-alkyl-RNA nucleotide moieties; and

2'-O—$C_1$-$C_6$-alkyloxy-$C_6$-$C_{26}$-aryl-RNA nucleotide moieties.

11. The oligonucleotide according to claim 10, wherein less than 30% of the total number of nucleotide units in the oligonucleotide are hydrophobic nucleotide units.

12. The oligonucleotide according to claim 1, wherein the carboxylated 2'-amino LNA nucleotide unit of formula (1') is a nucleotide unit of formula (1") or (1'''):

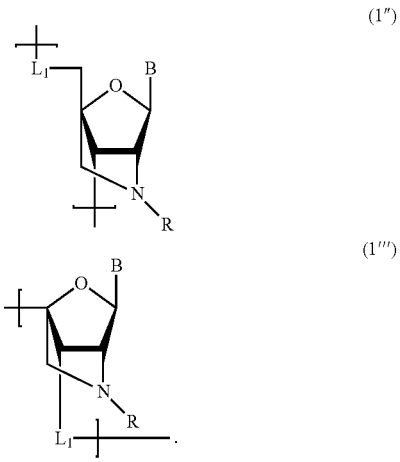

13. A method for transfecting cells, comprising mixing an oligonucleotide of claim 1 with an aqueous buffer and treating said cells with the mixture.

14. A pharmaceutical composition comprising an oligonucleotide of claim 1 and a pharmaceutically acceptable diluent, carrier or adjuvant.

15. The oligonucleotide according to claim 1, wherein said oligonucleotide comprises from 10 to 30 nucleotides and is single stranded.

16. An oligonucleotide, comprising from 3 to 100 nucleotide units, wherein at least one nucleotide unit independently comprises a 2'-amino locked nucleic acid (LNA) nucleotide of structure (11) to (16), wherein Y is oxygen, or Y is absent when the carbon attached to Y is a methylene group:

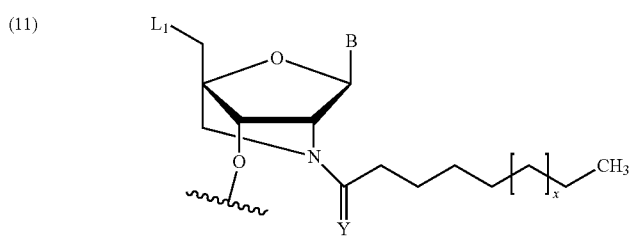

wherein x is 1, 2, 3, 4, 5, 7, 9, 11 or 13;

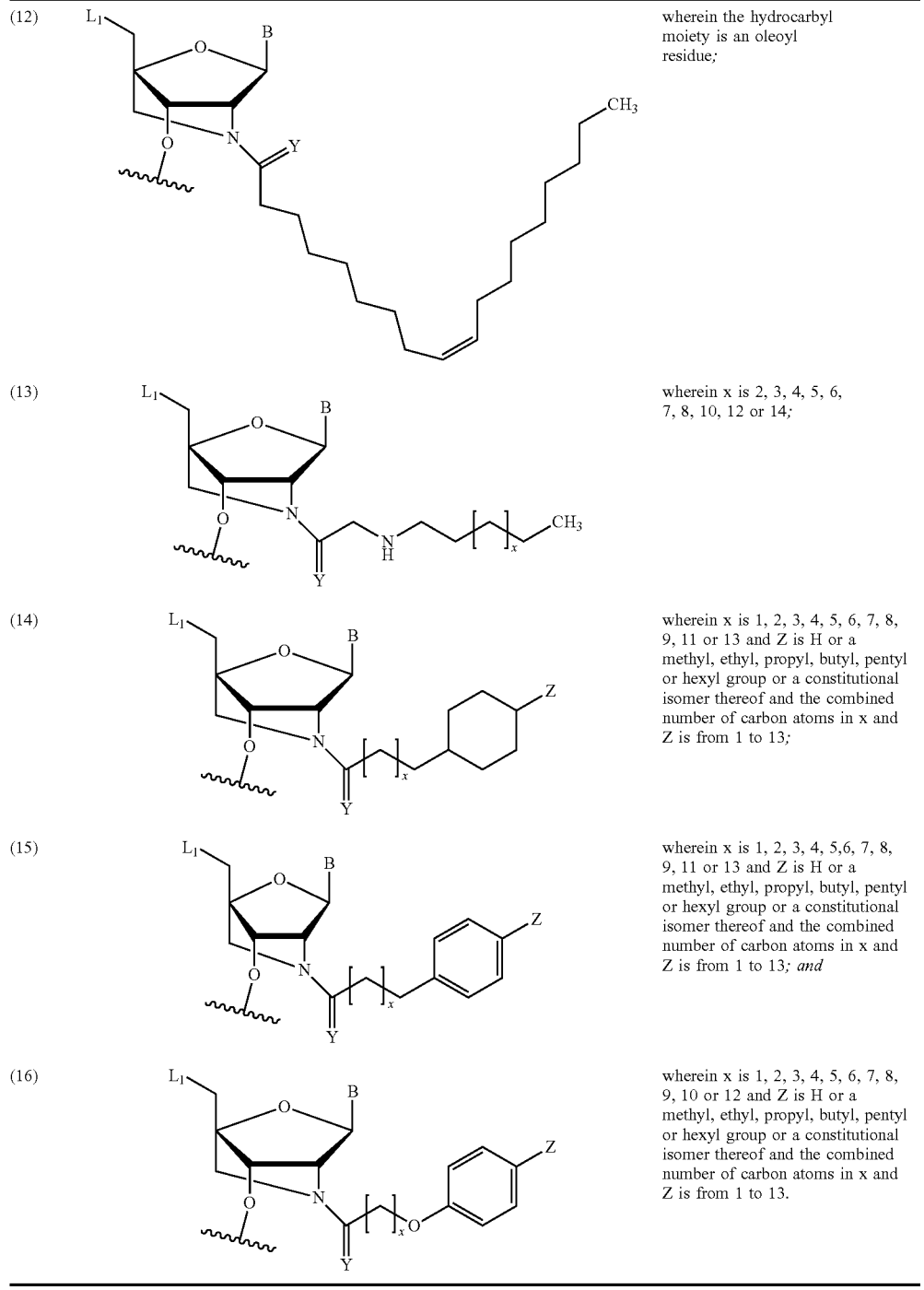

17. The oligonucleotide of claim 1, wherein less than 40% of the total number of nucleotide units in the oligonucleotide are carboxylated 2' amino LNA nucleotides.

18. The oligonucleotide of claim 1, wherein the combined portion of carboxylated 2' amino LNA nucleotides does not exceed 40% of all nucleotides of the oligonucleotide.

19. The oligonucleotide of claim 1, comprising a sequence that is identical or complementary to a sequence found in a genome.

20. The oligonucleotide of claim 1, wherein the carboxyalated 2' amino nucleotides are located close to the 5' and 3' ends of the oligonucleotide, from positions 1 to 5 from the 5' end of the oligonucleotide and/or positions t to (t−4) from its 3'-terminal end, wherein t designates the number of the 3'-terminal nucleotide counted from the 5'-terminal nucleotide unit of the oligonucleotide.

* * * * *